(12) United States Patent
Van Beurden

(10) Patent No.: US 8,731,882 B2
(45) Date of Patent: May 20, 2014

(54) METHODS AND APPARATUS FOR MODELING ELECTROMAGNETIC SCATTERING PROPERTIES OF MICROSCOPIC STRUCTURES AND METHODS AND APPARATUS FOR RECONSTRUCTION OF MICROSCOPIC STRUCTURES

(75) Inventor: Martijn Constant Van Beurden, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 770 days.

(21) Appl. No.: 12/877,905

(22) Filed: Sep. 8, 2010

(65) Prior Publication Data

US 2011/0218789 A1 Sep. 8, 2011

Related U.S. Application Data

(60) Provisional application No. 61/245,546, filed on Sep. 24, 2009.

(51) Int. Cl.

| | |
|---|---|
| G06G 7/56 | (2006.01) |
| G06F 17/10 | (2006.01) |
| G01B 11/02 | (2006.01) |
| G01B 11/30 | (2006.01) |
| G06F 17/50 | (2006.01) |
| G01R 15/00 | (2006.01) |

(52) U.S. Cl.
USPC ............. 703/5; 703/2; 356/498; 356/601; 716/53; 702/57

(58) Field of Classification Search
USPC ........................................... 703/2, 5
See application file for complete search history.

(56) References Cited

U.S. PATENT DOCUMENTS 5,588,032 A * 12/1996 Johnson et al. ............ 378/8
5,880,838 A * 3/1999 Marx et al. ............ 356/498

(Continued)

FOREIGN PATENT DOCUMENTS

EP   1 628 164 A2   2/2006

OTHER PUBLICATIONS

Article in J. Opt. Soc. Am. A/ vol. 22, No. 11/Nov. 2005 by Thore Magath et al "Fast iterative, coupled-integral-equation technique for inhomogeneous profiled and periodic slabs"; pp. 2405-2418.*

(Continued)

*Primary Examiner* — Akash Saxena
(74) *Attorney, Agent, or Firm* — Sterne, Kessler, Goldstein & Fox P.L.L.C.

(57) ABSTRACT

Improved convergence in the volume-integral method (VIM) of calculating electromagnetic scattering properties of a structure is achieved by numerically solving a volume integral equation for a vector field, F, rather than the electric field, E. The electric field, E, is determined from the vector field, F, after solving of the volume integral equation. The vector field, F, may be related to the electric field, E, by a change of basis, and may be continuous at material boundaries where the electric field, E, has discontinuities. Convolutions of the vector field, F, are performed using convolution operators according to the finite Laurent rule, which allows for efficient matrix-vector products using Fast Fourier Transforms. An invertible convolution-and-change-of-basis operator, C, is configured to transform the vector field, F, to the electric field, E, by performing a change of basis according to material and geometric properties of the periodic structure.

25 Claims, 17 Drawing Sheets

(56) References Cited

U.S. PATENT DOCUMENTS

| | | | |
|---|---|---|---|
| 6,097,488 A * | 8/2000 | Grek et al. | 356/364 |
| 6,377,041 B1 * | 4/2002 | Jones et al. | 324/244 |
| 6,795,801 B1 * | 9/2004 | Watkins et al. | 703/6 |
| 6,842,259 B2 * | 1/2005 | Rosencwaig et al. | 356/601 |
| 6,847,925 B2 * | 1/2005 | Ottusch et al. | 703/2 |
| 6,867,866 B1 * | 3/2005 | Chang et al. | 356/446 |
| 6,919,964 B2 * | 7/2005 | Chu | 356/601 |
| 7,038,850 B2 * | 5/2006 | Chang et al. | 359/446 |
| 7,710,572 B2 * | 5/2010 | Mos et al. | 356/448 |
| 8,255,849 B1 * | 8/2012 | Okhmatovski et al. | 716/110 |
| 2002/0113790 A1 * | 8/2002 | Hayashi | 345/426 |
| 2003/0147086 A1 * | 8/2003 | Rosencwaig et al. | 356/601 |
| 2003/0167156 A1 * | 9/2003 | Alba | 703/2 |
| 2004/0212810 A1 * | 10/2004 | Rosencwaig et al. | 356/601 |
| 2005/0122516 A1 * | 6/2005 | Sezginer et al. | 356/401 |
| 2005/0137809 A1 * | 6/2005 | Chang et al. | 702/27 |
| 2005/0286051 A1 * | 12/2005 | Sezginer et al. | 356/400 |
| 2007/0015993 A1 * | 1/2007 | Ciocan et al. | 600/407 |
| 2008/0069430 A1 * | 3/2008 | Setija et al. | 382/144 |
| 2008/0129986 A1 * | 6/2008 | Walsh | 356/138 |
| 2009/0103152 A1 * | 4/2009 | Szarvas et al. | 359/10 |
| 2011/0098992 A1 * | 4/2011 | Van Beurden et al. | 703/2 |
| 2011/0218789 A1 * | 9/2011 | Van Beurden | 703/13 |
| 2013/0018585 A1 * | 1/2013 | Zhdanov et al. | 702/2 |
| 2013/0066597 A1 * | 3/2013 | Van Beurden | 703/1 |

OTHER PUBLICATIONS

Peter Götz, Thomas Schuster, Karsten Frenner, Stephan Rafler, and Wolfgang Osten, "Normal vector method for the RCWA with automated vector field generation," Optics Express, 16(22):17295-17301, Oct. 2008.

Evgeny Popov and Michel Nevière, "Maxwell equations in Fourier space: fast-converging formulation for diffraction by arbitrary shaped, periodic, anisotropic media," J. Opt. Soc. Am. A, 18(11):2886-2894, Nov. 2001.

Lifeng Li, "Use of Fourier series in the analysis of discontinuous periodic structures," J. Opt. Soc. Am. A, 13(9):1870-1876, Sep. 1996.

Philippe Lalanne, "Improved formulation of the coupled-wave method for two-dimensional gratings," J. Opt. Soc. Am. A, 14(7):1592-1598, Jul. 1997.

Lifeng Li, "New formulation of the Fourier modal method for crossed surface-relief gratings," J. Opt. Soc. Am. A, 14(10):2758-2767, Oct. 1997.

Thomas Schuster, Johannes Ruoff, Norbert Kerwien, Stephan Rafler, and Wolfgang Osten, "Normal vector method for convergence improvement using the RCWA for crossed gratings," J. Opt. Soc. Am. A, 24(9):2880 {2890, Sep. 2007.

Yia-Chung Chang, Guangwei Li, Hanyou Chu, and Jon Opsal, "Efficient finite-element, Green's function approach for critical-dimension metrology of three-dimensional gratings on multilayer films," J. Opt. Soc. Am. A, 23(3): 638-6454, Mar. 2006.

Melisew T. Belachew, Preconditioning Dense Complex Linear Systems from a VIM Discretization (Aug. 2009) (unpublished M.S. thesis, University of Technology Eindhoven) (on file with University of Technology Eindhoven, Netherlands).

Rafler, S., "Investigation of methods to set up the normal vector field for the Differential Method," Proc. of SPIE 6995: 1-9, Institut für Technische Optik, Struttgart, Germany (Apr. 2008).

Partial European Search Report directed to related European Patent Application No. 10 17 5689, European Patent Office, Munich, Germany, mailed Mar. 10, 2011; 7 pages.

English-Language Translation of Notification of Reason(s) for Refusal directed to related Korean Patent Application No. 10-2010-0092926, mailed Oct. 8, 2013; 6 pages.

Van Beurden, M.C., et al., "Electromagnetic Modelling of Antennas Mounted on a Band-Gap Slab—Discretisation Issues and Domain and Boundary Integral Equations," Proceedings of the International Conference on Electromagnetics in Advanced Applications ICEAA '03; pp. 637-640.

* cited by examiner

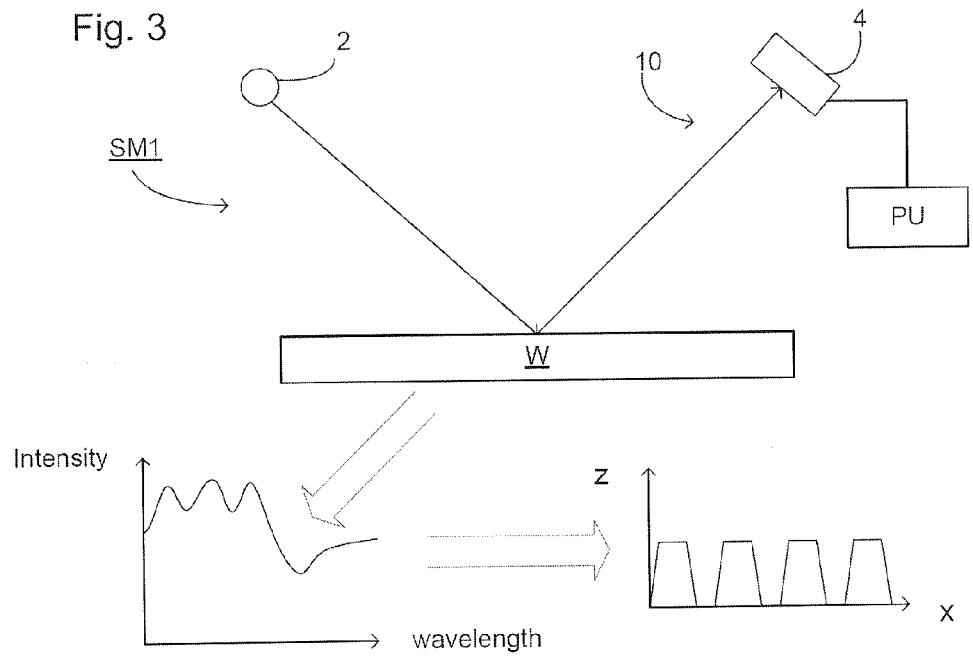
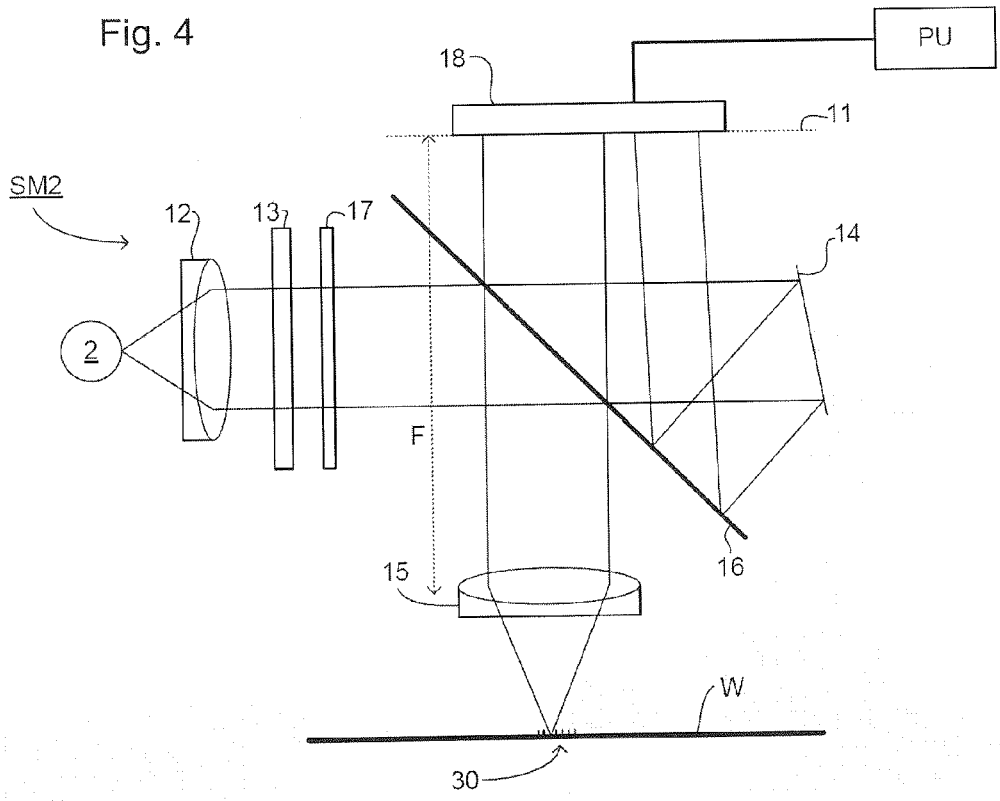

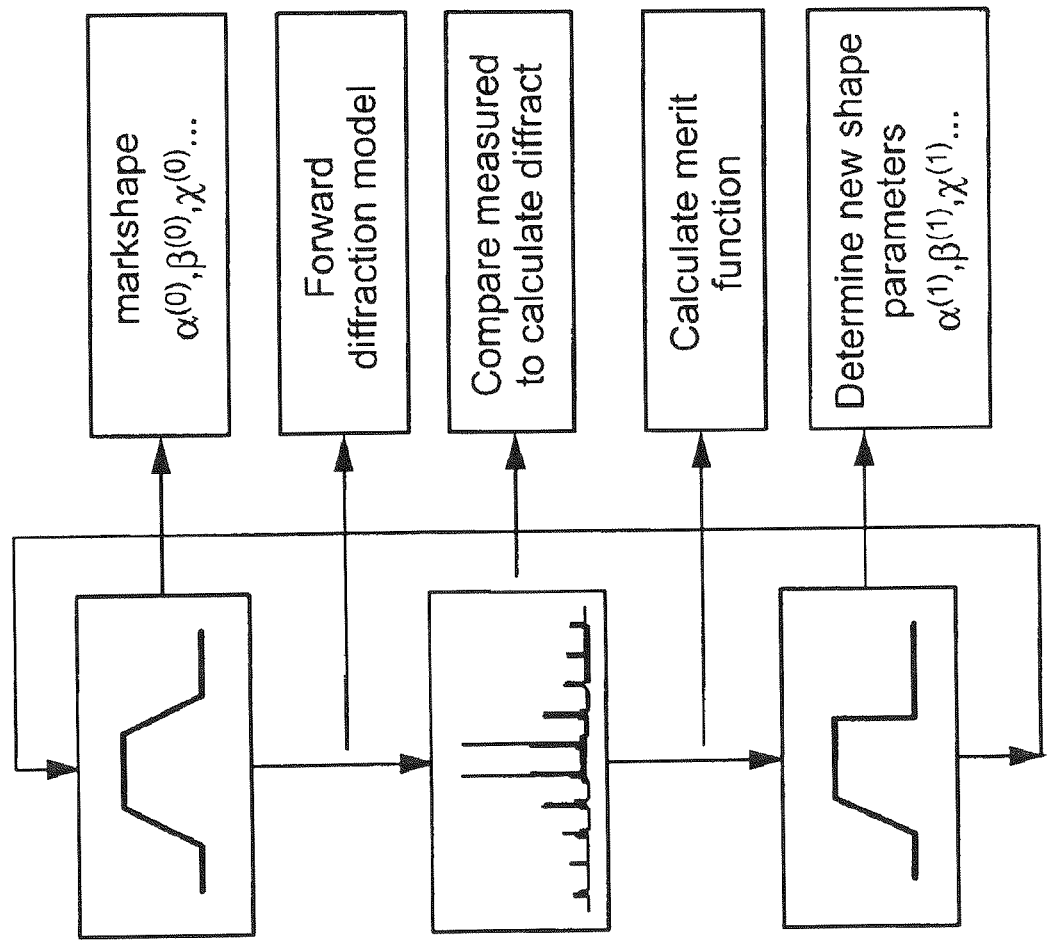
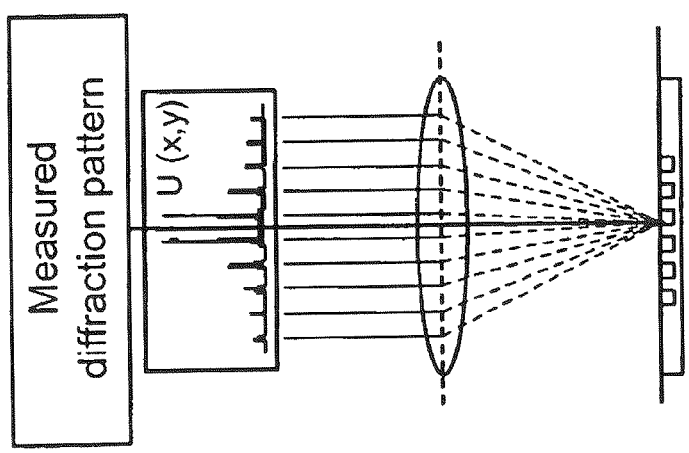
Fig. 5

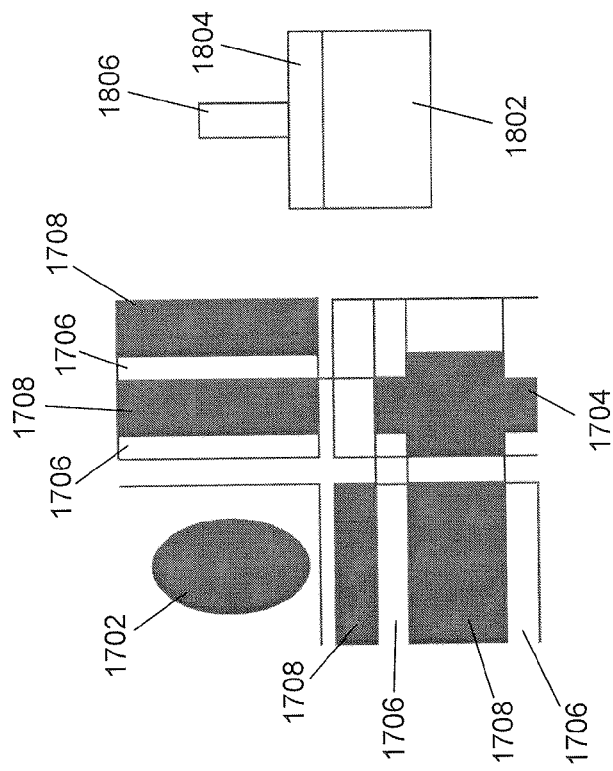
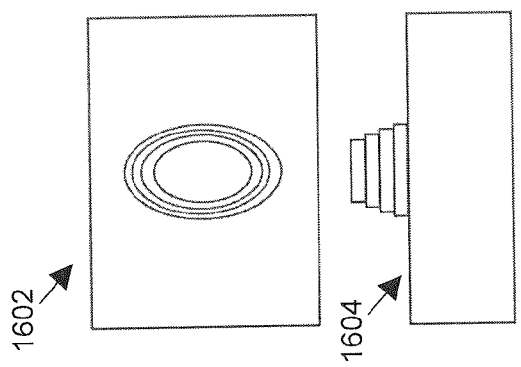
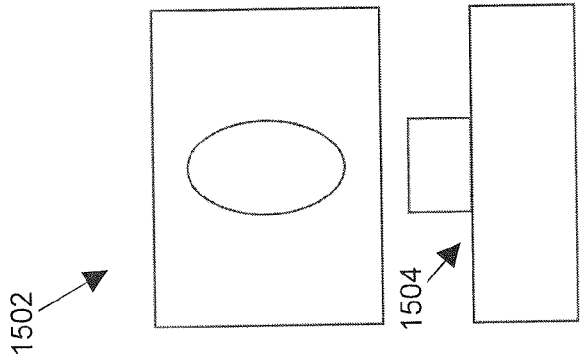

METHODS AND APPARATUS FOR MODELING ELECTROMAGNETIC SCATTERING PROPERTIES OF MICROSCOPIC STRUCTURES AND METHODS AND APPARATUS FOR RECONSTRUCTION OF MICROSCOPIC STRUCTURES

CROSS REFERENCE TO RELATED APPLICATIONS

This application claims priority under 35 U.S.C. §119(e) to U.S. Provisional Patent Application No. 61/245,546, filed Sep. 24, 2009, which is incorporated by reference herein in its entirety.

BACKGROUND

1. Field of the Invention

The present invention relates to numerical calculation of electromagnetic scattering properties of periodic structures. The invention may be applied for example in metrology of microscopic structures, for example to assess critical dimensions (CD) performance of a lithographic apparatus.

2. Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

More generally, it would be useful to be able to compare the scattered radiation with scattering behaviors predicted mathematically from models of structures, which can be freely set up and varied until the predicted behavior matches the observed scattering from a real sample. Unfortunately, although it is in principle known how to model the scattering by numerical procedures, the computational burden of the known techniques renders such techniques impractical, particularly if real-time reconstruction is desired, and/or where the structures involved are more complicated than a simple structure periodic in one-dimension.

SUMMARY

It is desirable in the field of semiconductor processing to rapidly perform accurate numerical calculations of electromagnetic scattering properties of periodic structures.

According to a first aspect of the invention, there is provided a method of calculating electromagnetic scattering properties, such as reflection coefficients, of a structure, the structure being periodic in at least one direction, x, y, and including materials of differing properties such as to cause a discontinuity in an electromagnetic field, E, at a material boundary, the method comprising numerically solving a volume integral equation for a vector field, F, that is related to the electromagnetic field, E, by a change of basis, the vector field, F, being continuous at the material boundary, so as to determine an approximate solution of the vector field, F.

The vector field, F, may be represented by at least one finite Fourier series with respect to the at least one direction, x, y, and the step of numerically solving the volume integral equation may comprise determining a component of the electromagnetic field, E, by convolution of the vector field, F, with a convolution-and-change-of-basis operator, C.

According to a second aspect of the invention, there is provided method of reconstructing an approximate structure of an object from a detected electromagnetic scattering property arising from illumination of the object by radiation, the method comprising the steps: estimating at least one object structure; determining at least one model electromagnetic scattering property from the at least one estimated object structure; comparing the detected electromagnetic scattering property to the at least one model electromagnetic scattering property; and determining an approximate object structure based on the result of the comparison, wherein the model electromagnetic scattering property is determined using the method according to the first aspect.

According to a third aspect of the invention, there is provided an inspection apparatus for reconstructing an approximate structure of an object, the inspection apparatus comprising: an illumination system configured to illuminate the object with radiation; a detection system configured to detect an electromagnetic scattering property arising from the illumination: a processor configured to: estimate at least one object structure; determine at least one model electromagnetic scattering property from the at least one estimated object structure; compare the detected electromagnetic scattering property to the at least one model electromagnetic scattering property; and determine an approximate object structure from a difference between the detected electromagnetic scattering property and the at least one model electromagnetic scattering property, wherein the processor is configured to determine the model electromagnetic scattering property using the method according to the first aspect.

According to a fourth aspect of the invention, there is provided a computer program product containing one or more sequences of machine-readable instructions for calculating electromagnetic scattering properties of a structure, the instructions being adapted to cause one or more processors to perform the method according to the first aspect.

According to a fifth aspect of the invention, there is provided a method of calculating electromagnetic scattering properties of a structure, the structure being periodic in at least one direction, x, y, and including materials of differing properties such as to cause a discontinuity in an electromagnetic field, E, at a material boundary, the method including numerically solving a volume integral equation for a vector field, F, that is related to and different from the electromagnetic field, E, so as to determine an approximate solution of the vector field, F.

According to a sixth aspect of the invention, there is provided method of reconstructing an approximate structure of an object from a detected electromagnetic scattering property arising from illumination of the object by radiation, the method comprising the steps: estimating at least one object structure; determining at least one model electromagnetic scattering property from the at least one estimated object structure; comparing the detected electromagnetic scattering property to the at least one model electromagnetic scattering property; and determining an approximate object structure based on the result of the comparison, wherein the model electromagnetic scattering property is determined using the method according to the fifth aspect. According to a seventh aspect of the invention, there is provided an inspection apparatus for reconstructing an approximate structure of an object, the inspection apparatus comprising: an illumination system configured to illuminate the object with radiation; a detection system configured to detect an electromagnetic scattering property arising from the illumination: a processor configured to: estimate at least one object structure; determine at least one model electromagnetic scattering property from the at least one estimated object structure; compare the detected electromagnetic scattering property to the at least one model electromagnetic scattering property; and determine an approximate object structure from a difference between the detected electromagnetic scattering property and the at least one model electromagnetic scattering property, wherein the processor is configured to determine the model electromagnetic scattering property using the method according to the fifth aspect. According to an eighth aspect of the invention, there is provided a computer program product containing one or more sequences of machine-readable instructions for calculating electromagnetic scattering properties of a structure, the instructions being adapted to cause one or more processors to perform the method according to the fifth aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 3 depicts a first scatterometer.

FIG. 4 depicts a second scatterometer.

FIG. 5 depicts a generic process for reconstruction of a 1-dimensional periodic diffraction grating from scatterometer measurements.

FIG. 15 depicts a top and side view of a binary grating cell with an elliptical cross section.

FIG. 16 depicts a top and side view of a staircased grating cell with elliptical cross section.

FIG. 17 depicts a procedure to approximate an ellipse by a staircased approximation.

FIG. 18 depicts a benchmark model structure.

Figure 1:
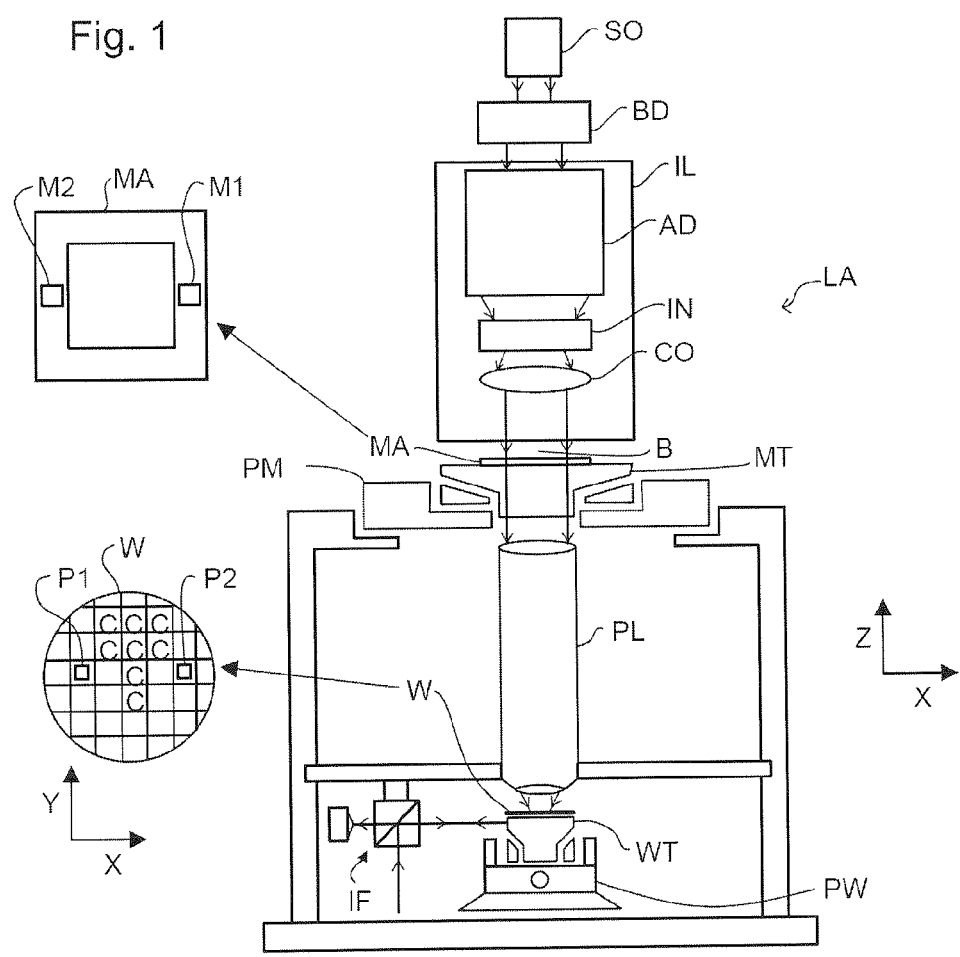
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
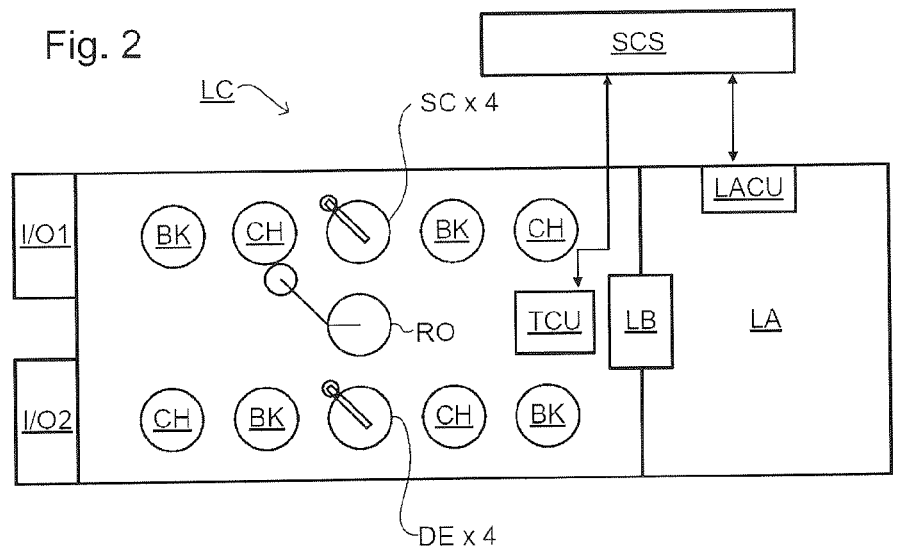
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions that are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer which may be used in an embodiment of the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU. In prior art scatterometers this can be done by Rigorous Coupled Wave Analysis (RCWA) and non-linear regression or by comparison with a library of simulated spectra as shown at the bottom of FIG. 3. In the scatterometer according to the invention Vector Integral equations are used. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer that may be used in an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate or aligned or not. CD uniformity is simply a measurement of the uniformity of the grating on the spectrum to determine how the exposure system of the lithographic apparatus is functioning. Specifically, CD, or critical dimension, is the width (e.g., the width of the target shown in FIG. 5) of the object that is "written" on the substrate and is the limit at which a lithographic apparatus is physically able to write on a substrate.

The way the measurement of the target shape (also referred to as the markshape) is typically carried out for 1D-periodic structures is as follows, with reference to FIG. 5: The target shape is estimated. This estimated shape is given different parameters such as $\alpha(0)$, $\beta(0)$, $\chi(0)$, and so on. Each of these parameters may be, for example, the angle of each side wall, the height of the top of the target, the width at the top of the target, the width at the bottom of the target, etc.

Typically, in prior art devices, a rigorous optical diffraction method such as RCWA is used to calculate the scattering properties, such as an estimated or model diffraction pattern of the estimated target shape. Other electromagnetic scattering properties such as estimated or model reflection or transmission coefficients may be used in place of or to obtain the estimated or model diffraction pattern.

The diffraction pattern of the actual target on the substrate is then measured by illuminating the target on the substrate with a radiation beam and detecting the diffracted beam, the pattern of which will be dependent on the properties of the target. This measured diffraction pattern and the model diffraction pattern are forwarded to a calculation system such as a computer.

The measured diffraction pattern and the model diffraction pattern are then compared and any differences are fed into a "merit function" calculation.

Using the merit function, which relates the sensitivity of certain target parameters to the shape of the diffraction pattern, new shape parameters are estimated. This may give a shape that is closer to the bottom shape of FIG. 5 which has new parameters such as α(0), β(1), χ(1), etc. These may be fed back iteratively into step 1 and steps 1 to 5 iterated until the desired accuracy is attained, thereby determining an approximate object structure.

The computation time of this iterative process is largely determined by the forward diffraction model, i.e., the calculation of the estimated model diffraction pattern using a rigorous optical diffraction theory from the estimated target shape.

A plurality of model diffraction patterns for different estimated target shapes may be calculated and stored in a library in step 2. Then in step 4 the measured diffraction pattern is compared to the model diffraction patterns in the library generated in step 2. If a match is found then the estimated target shape used to generate the matching library pattern can be determined to be the approximate object structure. Therefore iteration may not be needed if a library is used and a match is found. Alternatively a library search may be used to determine a course set of shape parameters, followed by one or more iteration using the merit function to determine a more accurate set of shape parameters so as to determine the approximate object structure.

For CD reconstruction of 2D-periodic structures RCWA is commonly used in the forward diffraction model, while the Volume Integral Method (VIM), Finite-difference time-domain (FDTD), and Finite element method (FEM) have also been reported.

Within RCWA, a spectral discretization scheme is used. To improve the convergence of this spectral discretization, the so-called Li rules are applied [3,4]. Alternatively, a normal-vector field formalism [6] can be used to improve the convergence of the spectral discretization [7,8].

One of the major problems of RCWA is that it requires a large amount of central processing unit (CPU) time and memory for 2D periodic structures, since a sequence of eigenvalue/eigenvector problems need to be solved and concatenated. For FDTD and FEM, CPU time is typically also too high.

Existing Volume Integral Methods (as disclosed in [2], U.S. Pat. No. 6,867,866 B1 and U.S. Pat. No. 7,038,850 B2, which are both incorporated by reference herein in their entireties) are based either on fully spatial discretization schemes that exhibit slow convergence with respect to mesh refinement or on spectral discretization schemes that exhibit poor convergence with respect to an increasing number of harmonics. As an alternative, a spectral discretization scheme that incorporates a heuristic method to improve the convergence has been proposed [2].

The linear system that has to be solved for VIM is much larger compared to RCWA, but if it is solved in an iterative way, only the matrix-vector product is needed together with the storage of several vectors. Therefore, the memory usage is typically much lower than for RCWA. The potential bottleneck is the speed of the matrix-vector product itself. If the Li rules were to be applied in VIM, then the matrix-vector product would be much slower, due to the presence of several inverse sub-matrices. Alternatively, the Li rules can be ignored and FFTs can be used to arrive at a fast matrix-vector product, but the problem of poor convergence remains.

The present invention relates to embodiments of an improved volume integral method (VIM). Realistic 2D-periodic CD reconstructions on resist gratings have been demonstrated using an embodiment of the present invention to be between 10 to 100 times faster than RCWA, while memory usage is from 10 to 100 times less than RCWA. Before the invention is described in detail, results are presented with reference to FIGS. 6 and 7 that illustrate the speed improvements provided by the present invention.

Figure 6:
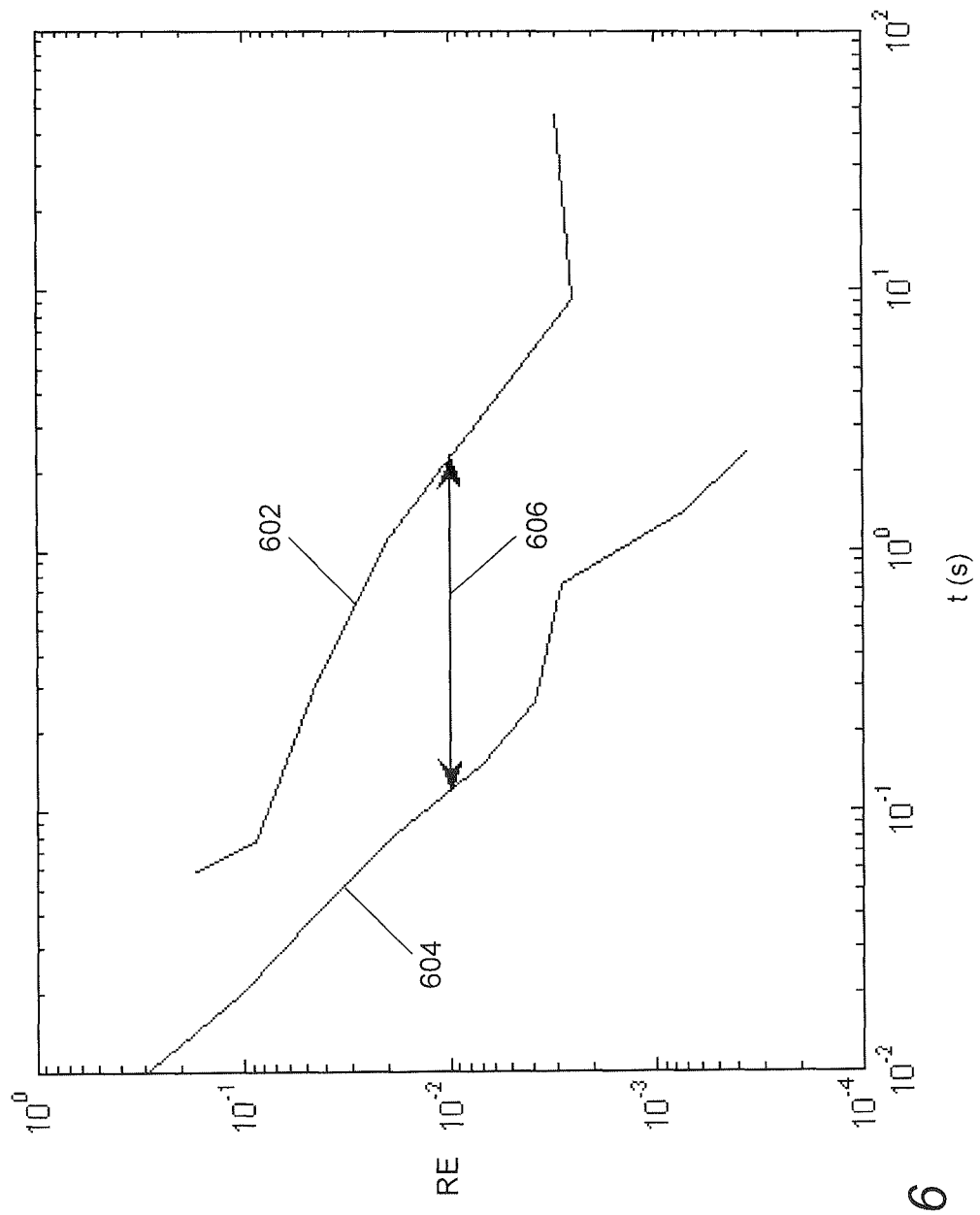
FIG. 6 depicts a graph illustrating the accuracy versus processing time for conventional rigorous coupled wave analysis (RCWA) and the volume integral method (VIM) according to an embodiment of the present invention for a modeled resist structure.

FIG. 6 shows a graph illustrating the accuracy versus processing time for conventional RCWA 602 and the volume integral method (VIM) 604 according to an embodiment of the present invention. FIG. 6 shows the results of models of the first order reflection coefficient with a resist structure. The vertical axis is the relative error, RE, given by $|R_p - R_p^*|/|R_p^*|$ where $R_p$ is the reflection coefficient for parallel polarization (where the electric field is parallel to the plane of incidence) and $R_p^*$ is the converged solution of RCWA with sufficient modes to achieve a five digit accuracy. The horizontal axis is central processing unit (CPU) time, t, in seconds, which is the time for one solve of the linear system corresponding to the VIM formula. The graph 602 of results for RCWA shows a greater CPU time than results for VIM according to an embodiment of the present invention shown by the graph 604. For example, at a relative error of $10^{-2}$ there is a factor of 20 improvement in CPU time afforded by this embodiment of present invention, as indicated by arrow 606. Therefore FIG. 6 shows that across the whole range of relative error (or accuracy) the present invention may lead to reduced CPU time for calculating one solution. The reduction in CPU time is very important for practical application of the present invention. Typically the aim would be to complete typically 14,000 solves in about one second. One second is the target because that is the time to perform successive scatterometry measurements on wafers in a production environment. By completing the calculations in such a short time it is possible to perform real-time analysis without slowing down the wafer production processes. The number 14,000 comes from 180 scattering angles times the number of parameters in the model to be varied (6 or 7) times 2 independent polarizations of the incident wave times 6 nonlinear solves for estimation of the real shape of the target. The data in FIG. 6 is derived from the same data set as used to derive the data presented in FIGS. 21 and 22 that are discussed below.

Figure 7:
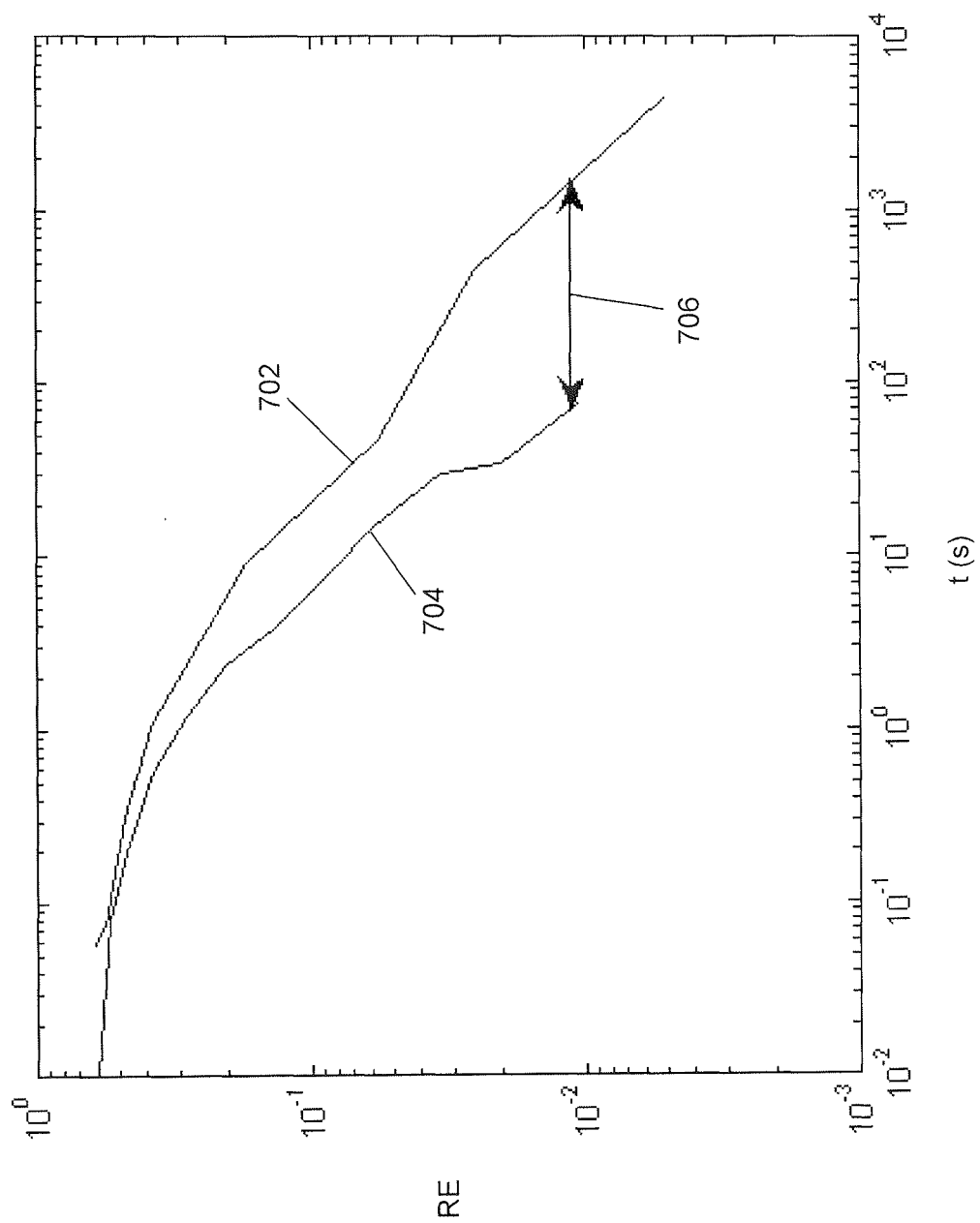
FIG. 7 depicts similar data to that shown in FIG. 6 but for a modeled silicon structure.

FIG. 7 shows graphs of similar data to that shown in FIG. 6 but for a modeled silicon structure and the zeroth order reflection coefficient. The same axes are used except the vertical relative error axis covers a narrower range and the horizontal time axis covers a wider range. Graph 702 is the RCWA result and graph 704 is the result using VIM according to an embodiment of the present invention. Again there is a factor of 20 improvement over RCWA afforded by the present invention, as shown by arrow 706, for a $10^{-2}$ relative error.

Figure 8:
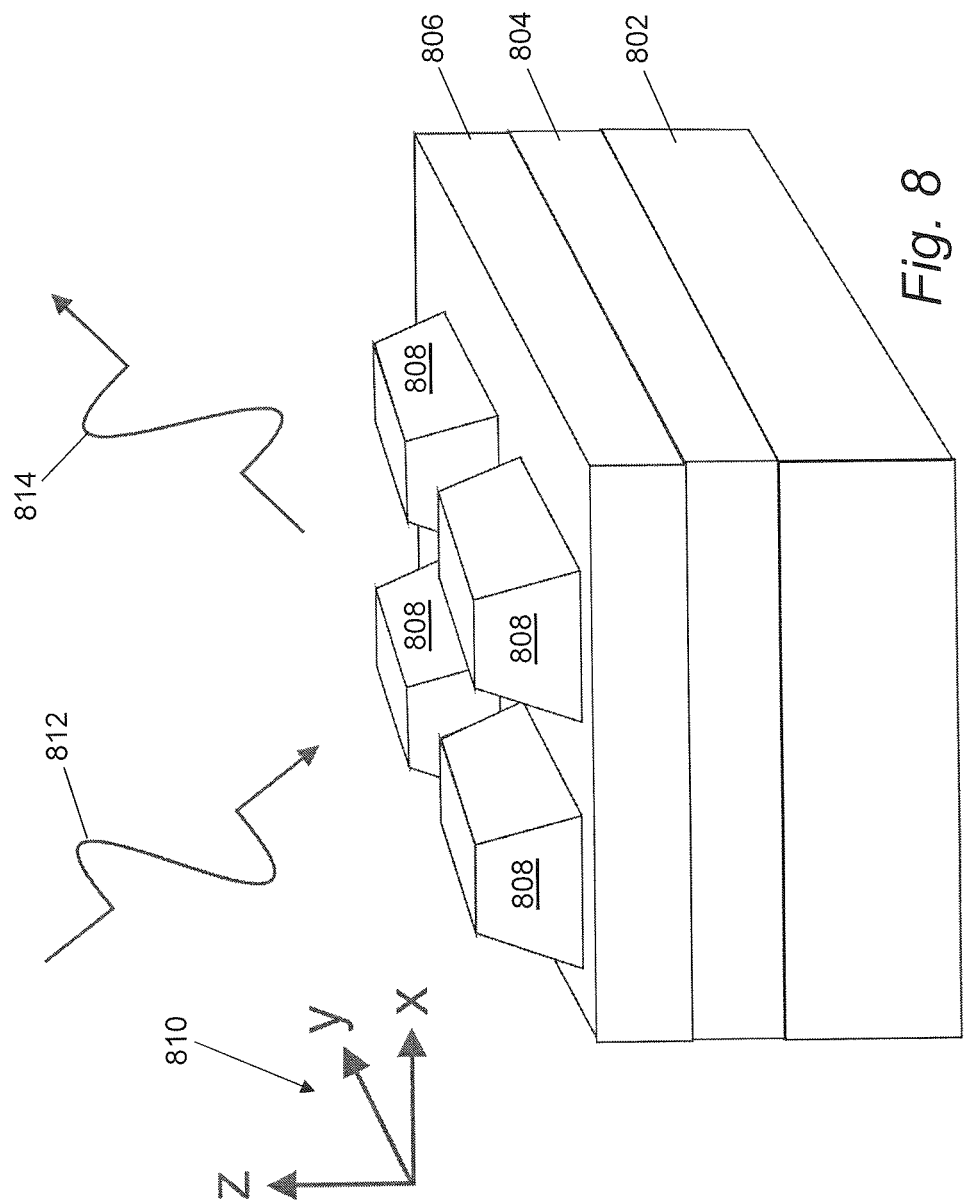
FIG. 8 depicts the scattering geometry that may be reconstructed in accordance with an embodiment of the present invention.

FIG. 8 illustrates schematically the scattering geometry that may be reconstructed in accordance with an embodiment of the present invention. A substrate 802 is the lower part of a medium layered in the z direction. Other layers 804 and 806 are shown. A two dimensional grating 808 that is periodic in x and y is shown on top of the layered medium. The x, y and z axes are also shown 810. An incident field 812 interacts with and is scattered by the structure 802 to 808 resulting in a reflected field 814. Thus the structure is periodic in at least one direction, x, y, and includes materials of differing properties such as to cause a discontinuity in an electromagnetic field, $E^{tot}$, that comprises a total of incident, $E^{inc}$, and scattered, $E^s$, electromagnetic field components at a material boundary between the differing materials.

Figure 9:
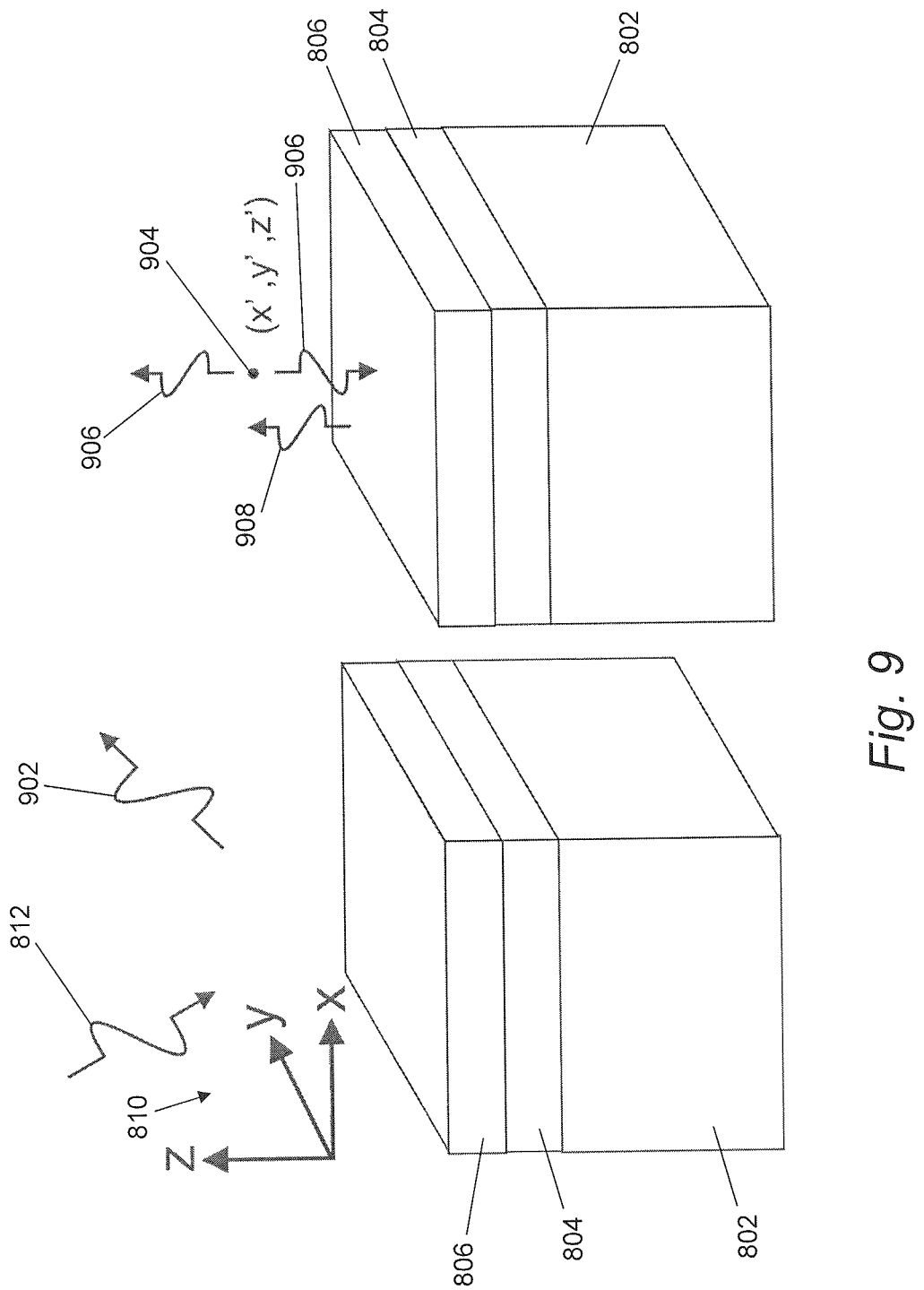
FIG. 9 depicts the structure of the background and illustrates use of a Green's function to calculate the interaction of the incident field with the layered medium.

FIG. 9 shows the structure of the background and schematically illustrates the Green's function that may be used to calculate the interaction of the incident field with the layered medium. The layered medium 802 to 806 is labeled the same as in FIG. 8. The x, y and z axes are also shown 810 along with the incident field 812. A directly reflected field 902 is also shown. The point source (x y', z') 904 represents the Green's function interaction with the background that generates a field 906. In this case because the point source 904 is above the top layer 806 there is only one background reflection 908 from the top interface of 806 with the surrounding medium. If the point source is within the layered medium then there will be background reflections in both up and down directions (not shown).

The VIM formula to be solved is $$E^{inc}(x,y,z) = E^{tot}(x,y,z) - \iiint \overline{G}(x,x',y,y',z,z') J^c(x',y',z') dx'dy'dz' \quad J^c(x',y',z') = \chi(x',y',z') E^{tot}(x',y',z')$$

In this equation, the incident field $E^{inc}$ is a known function of angle of incidence, polarization and amplitude, $E^{tot}$ is the total electric field that is unknown and for which the solution is calculated, $J^c$ is the contrast current density, $\overline{G}$ is the Green's function (a 3×3 matrix), $\chi$ is the contrast function given by $(\epsilon_r(x,y,z)/\epsilon_{r,bac}(z) - 1)$, where $\epsilon_r$ is the relative permittivity of the structure, $\epsilon_{r,bac}$ is the relative permittivity of the background medium. $\chi$ is zero outside the gratings.

The Green's Function $\overline{G}(x,x',y,y',z,z')$ is known and computable for the layered medium including 802 to 806. The Green's Function shows a convolution and/or modal decomposition $(m_1, m_2)$ in the xy plane and the dominant computation burden along the z axis in $\overline{G}$ are convolutions.

For discretization, the total electric field is expanded in Bloch/Floquet modes in the xy plane. Multiplication with x becomes: (a) discrete convolution in the xy plane (2D FFT); and (b) product in z. The Green's function interaction in the xy plane is an interaction per mode. The Green's function interaction in z is a convolution that may be performed with one-dimensional (1D) FFTs with a complexity O(N log N).

The number of modes in xy is $M_1 M_2$ and the number of samples in z is N.

The efficient matrix-vector product has a complexity $O(M_1 M_2 N \log(M_1 M_2 N))$ and the storage complexity is $O(M_1 M_2 N)$.

Figure 10:
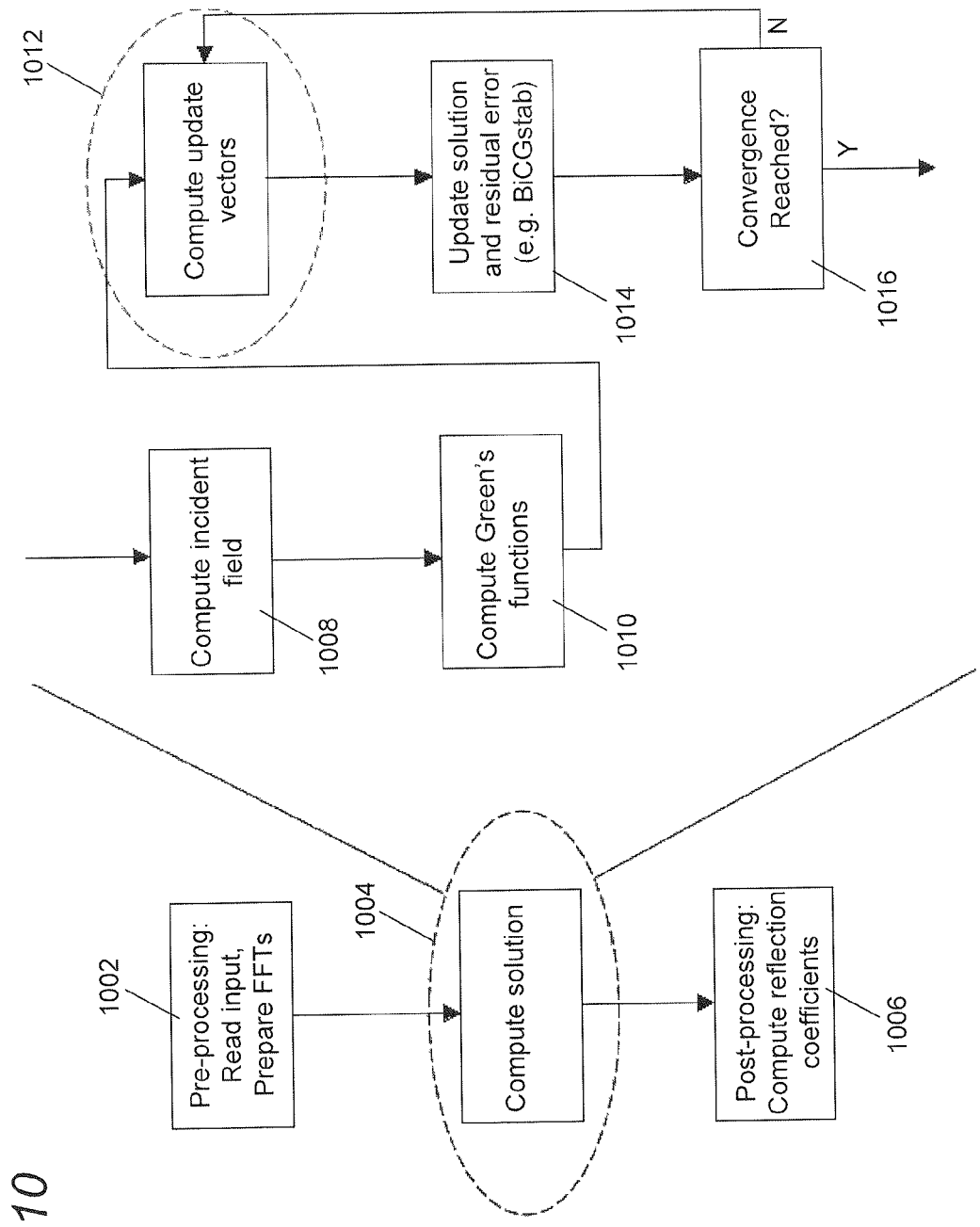
FIG. 10 is a flow chart of the high-level method of solving the linear system corresponding to the VIM formula.

The VIM solution method for Ax=b is performed using an iterative solver based on a Krylov subspace method, e.g., BiCGstab(1) (Stabilized BiConjugate Gradient method), in which typically has the steps:
Define residual error is defined as $r_n = b - A x_n$
Compute update vector(s) $v_n$ via residual error
Update solution: $x_{n+1} = x_n + a_n v_n$
Update residual error $r_{n+1} = r_n - a_n A v_n$ FIG. 10 is a flow chart of the high level method of solving the linear system corresponding to the VIM formula. This is a method of calculating electromagnetic scattering properties of a structure, by numerically solving a volume integral. At the highest level the first step is pre-processing 1002, including reading the input and preparing FFTs. The next step is to compute the solution 1004. Finally, post-processing 1006 is performed in which reflection coefficients are computed. Step 1004 includes various steps also shown at the right hand side of FIG. 10. These steps are computing the incident field 1008, computing the Green's Functions 1010, computing the update vectors 1012, updating the solution and residual error (e.g., using BiCGstab) 1014 and testing to see if convergence is reached 1016. If convergence is not reached control loops back to step 1012 that is the computation of the update vectors.

Figure 11:
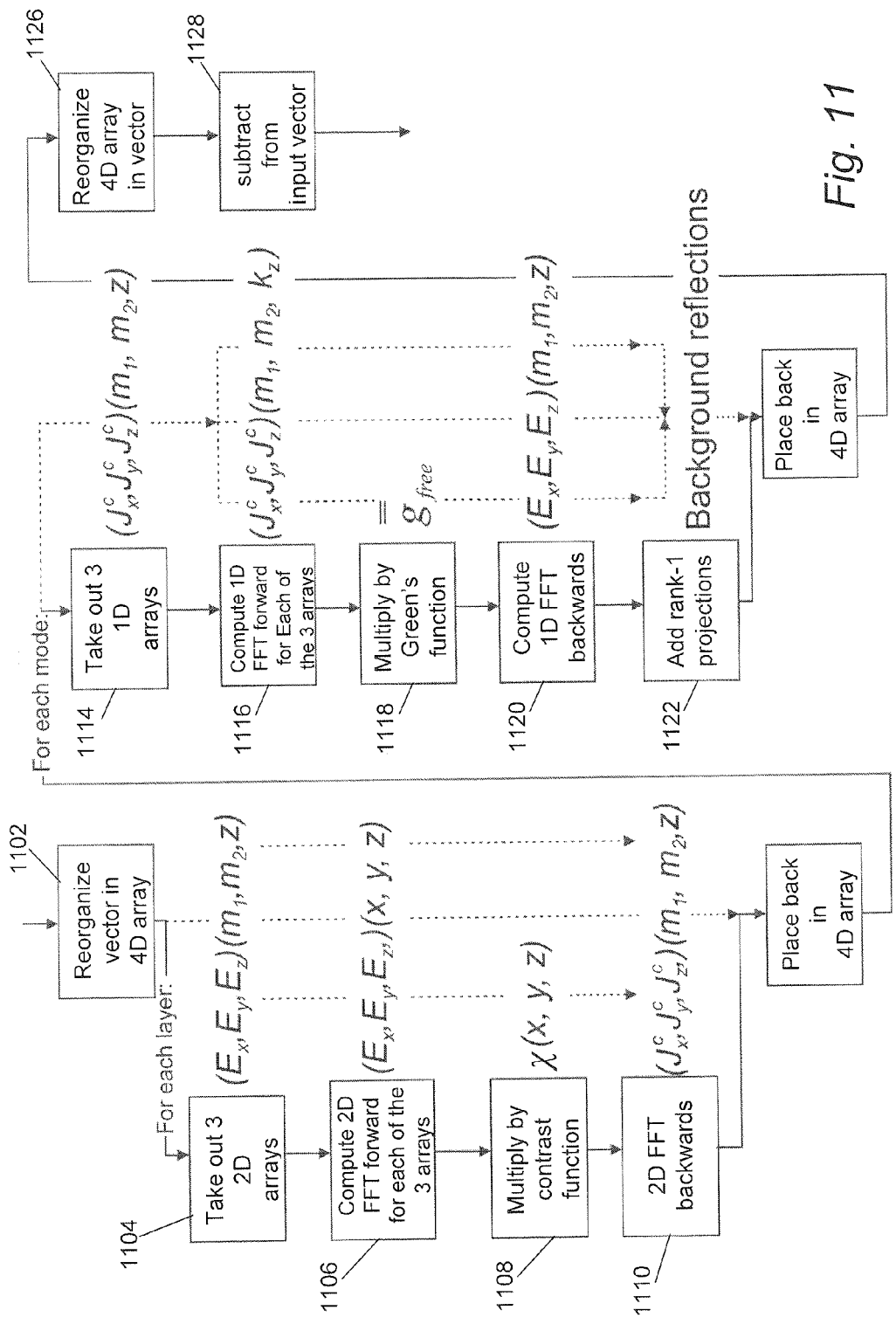
FIG. 11 is a flow chart of the computation of update vectors using the VIM formula as known in the prior art.

FIG. 11 illustrates the steps in computing update vectors corresponding to step 1012 of FIG. 10 using the volume integral method as known in the prior art, which is a method of calculating electromagnetic scattering properties of a structure, by numerically solving a volume integral equation for an electric field, E.

Step 1102 is reorganizing the vector in a four-dimensional (4D) array. In this array the first dimension has three elements $E_x$, $E_y$ and $E_z$. The second dimension has elements for all values of $m_1$. The third dimension has elements for all values of $m_2$. The fourth dimension has elements for each value of z. Thus the 4D array stores the spectral (in the xy plane) representation of the total electric field $(E_x, E_y, E_z)(m_1, m_2, z)$. The three parallel dotted arrows descending from step 1102 in FIG. 11 correspond to the processing of three 2D arrays, one each for $E_x$, $E_y$ and $E_z$ respectively, by steps 1104 to 1110 carried out for each layer, z. These steps perform the convolution of the spectral (in the xy plane) representation of the electric field $(E_x, E_y, E_z)(m_1, m_2, z)$ with the material properties to calculate the spectral (in the xy plane) representation of the contrast current density corresponding to Equation (1.3) below. In detail, step 1104 involves taking out the three 2D arrays (the two dimensions being for $m_1$ and $m_2$). In step 1106 a 2D FFT is computed forward for each of the three arrays into the spatial domain. In step 1108 each of the three arrays is multiplied by the spatial representation of the contrast function $\chi(x,y,z)$ that is filtered by the truncation of the Fourier representation. The convolution is completed in step 1110 with the 2D FFT backwards into the spectral (in the xy plane) domain yielding the spectral contrast current density $(J_x^c, J_y^c, J_z^c)(m_1, m_2, z)$. In step 1112 the calculated spectral contrast current density is placed back into the 4D array.

Then for each mode (i.e., for all sample points in z, at the same time), steps 1114 to 1122 are performed. The three dotted parallel arrows descending from beside step 1116 correspond to computing the integral term in Equation (1.1) below, which is the background interaction with the contrast current density that has itself arisen from the total electric field's interaction with the structure. This is performed by a convolution of $(J_x^c, J_y^c, J_z^c)(m_1, m_2, z)$ with the spatial (with respect to the z direction) Green's function, using a multiplication in the spectral domain (with respect to the z direction).

In detail, in step 1114 the spectral contrast current density $(J_x^c, J_y^c, J_z^c)(m_1, m_2, z)$ is taken out as three 1D arrays for each of x, y, and z. In step 1116, the convolution begins by computing the 1D FFT forward for each of the three arrays into the spectral domain with respect to the z direction to produce $(J_x^c, J_y^c, J_z^c)(m_1, m_2, k_z)$, where $k_z$ is the Fourier variable with respect to the z direction. In step 1118 the truncated Fourier transform of the contrast current density is multiplied in the spectral domain (with respect to the z direction) by the Fourier transform of the spatial Green's function $\overline{g}_{free}$. In step 1120 a 1D FFT backwards is performed into the spatial domain with respect to the z direction. In step 1122 background reflections (see 908 in FIG. 9) in the spatial domain with respect to z are added. This separation of the background reflections from the Green's function is a conventional technique and the step may be performed by adding rank 1 projections as will be appreciated by one skilled in the art. As each mode is processed then the update vectors for the total electric field, $(E_x, E_y, E_z)(m_2, m_2, z)$, thus calculated are placed back into the 4D array in step 1124.

The next step is reorganizing the 4D array in a vector 1126, which is different from step 1102 "reorganizing the vector in a 4D array", in that it is the reverse operation: each one-dimensional index is uniquely related to a four-dimensional index. Finally in step 1128 the vector output from step 1126 is subtracted from the input vector, corresponding to the subtraction in the right-hand side of Equation (1.1). The input vector is the vector that enters at step 1102 in FIG. 11 and contains $(E_x, E_y, E_z)(m_2, m_2, z)$.

A problem with the method described in FIG. 11 is that it leads to poor convergence, as is demonstrated below with reference to FIG. 19 that shows a plot of convergence using the method of FIG. 10 relative to RCWA results. This poor convergence is caused by concurrent jumps in permittivity and electric field for the truncated Fourier-space representation. As discussed above, in the VIM method the Li inverse rule is not suitable for overcoming the convergence problem because in VIM the complexity of the inverse rule leads to a very large computational burden because of the very large number of inverse operations that are needed in the VIM numerical solution. Embodiments of the present invention overcome the convergence problems caused by concurrent jumps without resorting to use of the inverse rule as described by Li. By avoiding the inverse rule the present invention does not sacrifice the efficiency of the matrix vector product that is required for solving the linear system in an iterative manner in the VIM approach.

Figure 12:
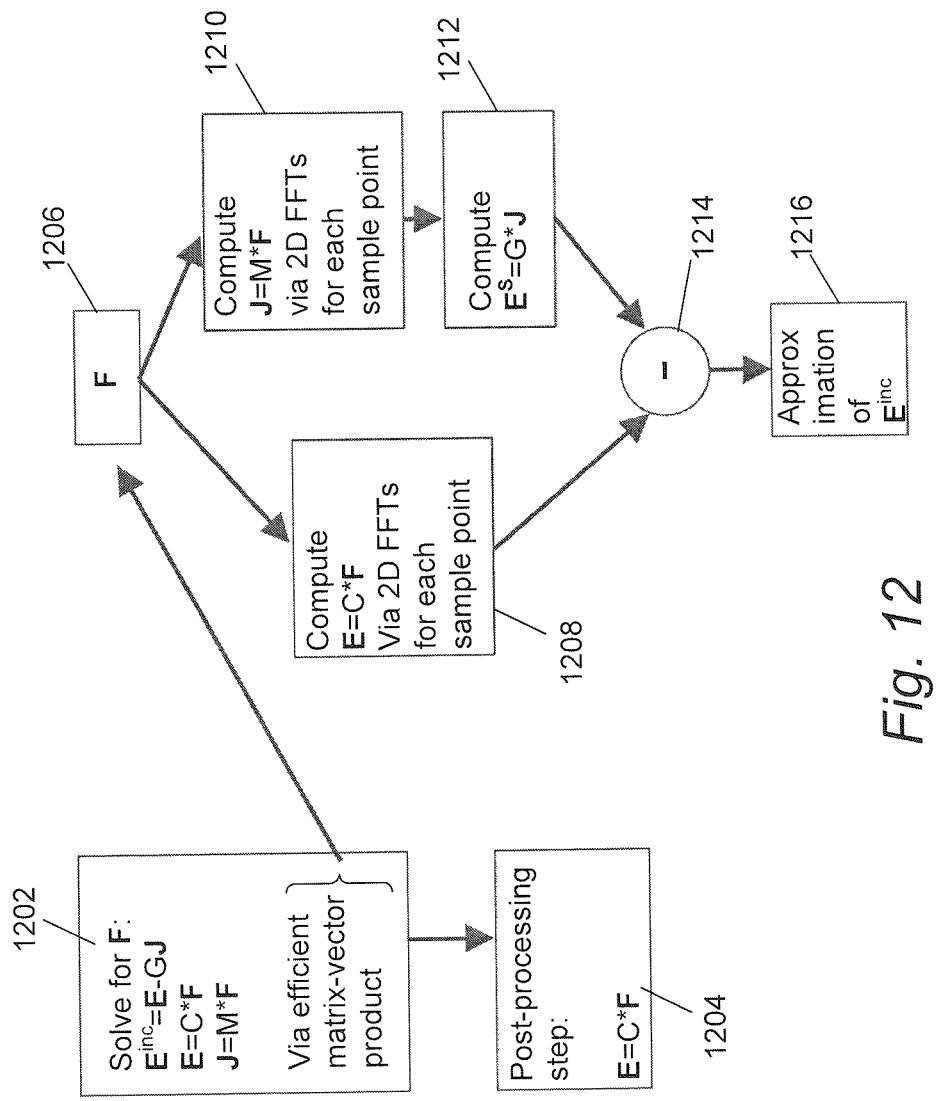
FIG. 12 depicts an embodiment of the present invention using a continuous vector field to numerically solve the VIM formula.

FIG. 12 illustrates an embodiment of the present invention using a continuous vector field to numerically solve the VIM formula. This involves numerically solving a volume integral equation for a vector field, F, that is related to the electric field, E, by a change of basis, the vector field, F, being continuous at one or more material boundaries, so as to determine an approximate solution of the vector field, F. The vector field, F, is represented by at least one finite Fourier series with respect to at least one direction, x, y, and the step of numerically solving the volume integral equation comprises determining a component of the electric field, E, by convolution of the vector field, F, with a convolution-and-change-of-basis operator, C, and determining a current density, J, by convolution of the vector field, F, with a convolution operator, M. The convolution-and-change-of-basis operator, C, is invertible and comprises material and geometric properties of the structure in at least one direction x, y and is configured to transform the vector field, F, to the electric field, E, by performing a change of basis according to the material and geometric properties. The convolution operator, M, comprises material and geometric properties of the structure in the at least one direction, x, y. The current density, J, may be a contrast current density and is represented by at least one finite Fourier series with respect to the at least one direction, x, y. The convolutions are performed using a transformation such as one selected from a set comprising a fast Fourier transform (FFT) and number-theoretic transform (NTT). The convolution-and-change-of-basis operator, C, and the convolution operator, M, operate according to a finite discrete convolution, so as to produce a finite result.

FIG. 12 shows the step 1202 of solving the VIM system for an intermediate vector field, F, with a post-processing step 1204 to obtain a total electric field, E, by convolution of the approximate solution of the vector field, F, with the convolution-and-change-of-basis operator, C. The convolution may be performed using a transformation such as one selected from a set comprising a fast Fourier transform (FFT) and number-theoretic transform (NTT). FIG. 12 also shows at the right hand side a schematic illustration of performing an efficient matrix-vector product 1206 to 1216 to solve the VIM system iteratively. This starts with an intermediate vector field, F, in step 1206. The first time that F is set up, it can be started from zero. After that initial step, the estimates of F are guided by the iterative solver and the residual. Next the total electric field, E, is computed 1208 using the convolution of a convolution-and-change-of-basis operator, C, with the intermediate vector field, F, via 2D FFTs for each sample point in the z direction. The convolution-and-change-of-basis operator, C, is configured to transform the basis of the intermediate vector field, F, to the basis of the total electric field, E. Also, the contrast current density, J, is computed in step 1210 using a convolution of a material convolution operator, M, with the intermediate vector field, F. Step 1210 is performed for each sample point in z with the convolution being performed via 2D FFTs. In step 1212 the convolutions and rank-1 projections between the Green's function, G, and the contrast current density, J, are computed to yield the scattered electric field, $E^s$. The convolution may be performed using a transformation such as one selected from a set comprising a fast Fourier transform (FFT) and number-theoretic transform (NTT). Operation 1214 subtracts the two computed results $E^s$ from E to obtain an approximation of $E^{inc}$ 1216. Steps 1202 and 1206 to 1216 correspond to Equation (1.4) as discussed below. Because steps 1206 to 1216 produce update vectors then the post-processing step 1204 is used to produce the final value of the total electric field, E.

Rather than a separate post-processing step 1204 the sum of all the update vectors may be recorded at step 1208 in order to calculate the total electric field, E. However, that approach increases the storage requirements of the method, whereas the post-processing step 1204 is not costly in storage or processing time, compared to the iterative steps 1206 to 1216.

Figure 13:
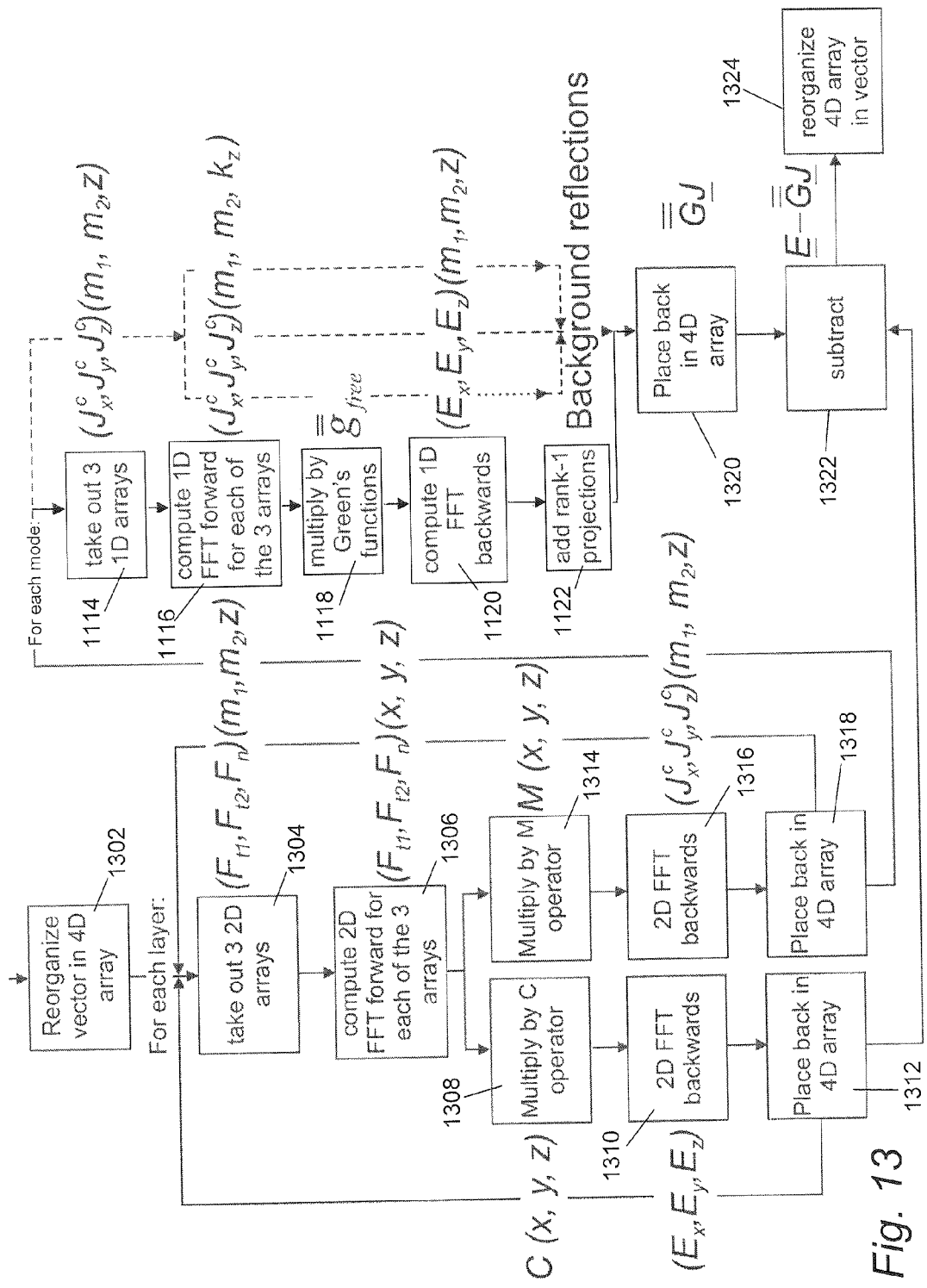
FIG. 13 is a flow chart of the computation of update vectors in accordance with an embodiment of present invention.

FIG. 13 is a flow chart of the computation of update vectors in accordance with an embodiment of present invention. The flow chart of FIG. 13 corresponds to the right hand side (steps 1206 to 1216) of FIG. 12.

In step 1302 the vector is reorganized in a 4D array. Then for each sample point in z, steps 1304 to 1318 are performed. In step 1304 three 2D arrays are taken out of the 4D array. These three 2D arrays $(F_{t1}, F_{t2}, F_n)(m_1, m_2, z)$ correspond respectively to the two tangential components $F_{t1}, F_{t2}$ and the normal component $F_n$ of the continuous vector field, F, (as described in Equation (2.44) below), each having the 2 dimensions corresponding to $m_1$ and $m_2$. Thus the vector field, F, is constructed from a combination of field components of the electromagnetic field, E, and a corresponding electromagnetic flux density, D, by using a normal-vector field, n, to filter out continuous components of the electromagnetic field, E, tangential to the at least one material boundary and also to filter out the continuous components of the electromagnetic flux density, D, normal to the at least one material boundary. In step 1306 the convolution of the spectral continuous vector field, represented by $(F_{t1}, F_{t2}, F_n)(m_1, m_2, z)$ begins with the computation in step 1306 of the 2D FFT forward into the spatial domain for each of the three arrays, represented by $(F_{t1}, F_{t2}, F_n)(x,y,z)$. In step 1308 the Fourier transform $(F_{t1}, F_{t2}, F_n)(x,y,z)$ obtained from step 1306 is multiplied in the spatial domain by the spatial multiplication operator C(x,y,z). In step 1310 the product obtained in step 1308 is transformed into the spectral domain by a 2D FFT backwards. The spectral total electric field, $(E_x, E_y, E_z)$, is then placed back in the 4D array at step 1312. Furthermore, a copy is fed forward to the subtract operation 1322 discussed below.

In step 1314 the Fourier transform $(F_{t1}, F_{t2}, F_n)(x,y,z)$ obtained from step 1306 is multiplied in the spatial domain by the multiplication operator, M. The product of the calculation in step 1314 is transformed in step 1316 by a 2D FFT backwards into the spectral domain to yield the spectral contrast current density, represented by $(J_x^c, J_y^c, J_z^c)(m_1, m_2, z)$ In step 1318 the spectral contrast current density, is placed back in the 4D array.

In order to complete the calculation of the approximation of the known incident electrical field, $E^{inc}$, the Green's function's interaction with the background is calculated for each mode, $m_1$, $m_2$, by steps 1114 to 1122 in the same manner as described with reference to the corresponding identically numbered steps in FIG. 11.

In step 1320 the resulting convolution of the spectral Green's function of the background, $\overline{G}$, and the spectral contrast current density, J, is placed back in the 4D array. Finally in step 1322 the calculation of the approximation of the known incident electrical field, $E^{inc}$, is completed with the subtraction of the result of step 1320 from the total electric field fed forward from step 1312 and the final step 1324 reorganizes the 4D array in a vector. The means every four-dimensional index of the 4D array is uniquely related to a one-dimensional index of the vector.

Figure 14:
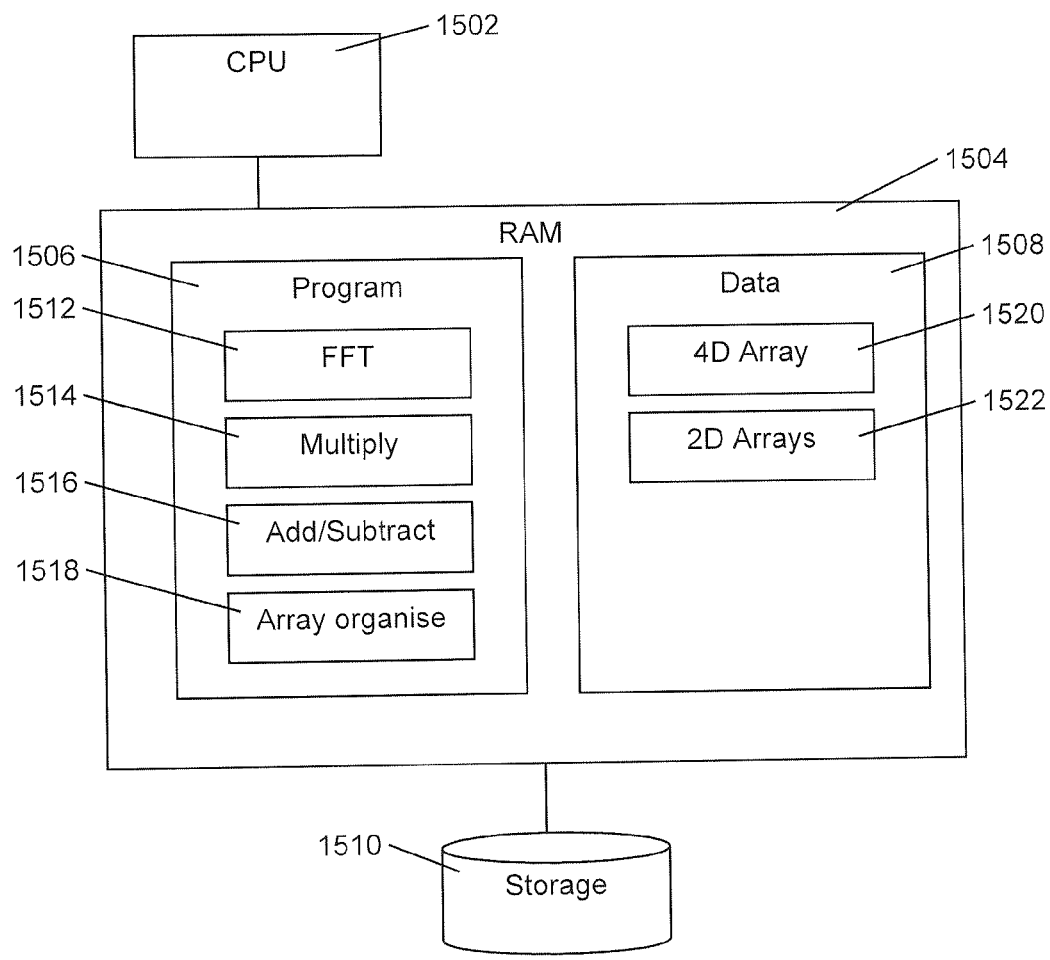
FIG. 14 depicts in schematic form a computer system configured with programs and data in order to execute VIM in accordance with an embodiment of the present invention.

FIG. 14 shows in schematic form a computer system configured with programs and data in order to execute a method in accordance with an embodiment to the present invention. The computer system comprises a central processing unit (CPU) 1502 and random access memory (RAM) 1504 which is used to store the program instructions 1506 and data 1508 during execution of the program. The computer system also includes disk storage 1510 that is used to store program instructions and data before and after the execution of the program.

The program instructions 1506 include Fast Fourier Transform routines 1512, matrix multiplication functions 1514, other arithmetic functions such as addition and subtraction 1516 and array organizing functions 1518. The data 1508 comprises the 4D array 1520 and 2D arrays 1522 used during calculation of the solution of the VIM system. Other conventional computer components for input and output are not shown.

FIG. 15 illustrates a top 1502 and side 1504 view of a binary grating cell with an elliptical cross section on a homogeneous half space.

FIG. 16 illustrates a top 1602 and side 1604 view of a staircased grating cell with elliptical cross section on a homogeneous half space.

FIG. 17 illustrates a procedure to approximate an ellipse 1702 by a staircased approximation 1704 in the transverse plane by introducing odd 1706 (white support) and even 1708 (solid/shaded support) projection operators per dimension. By multiplying a projection operator in one direction by a projection operator in the other direction, a pattern of isolated boxes appears. This allows for the construction of a continuous function that has the proper behavior on the support of each isolated box.

FIG. 18 illustrates a benchmark model structure. One cell of the grating is shown with a silicon substrate 1802, a Bottom Anti-Reflective Coating (BARC) 1804 and a resist grating element 1806.

The radiation and model parameters are:
Wavelength: $\lambda$=500 nm
Pitch x & y: $\lambda \times \lambda$=500 nm×500 nm
Footprint: $0.15\lambda \times 0.15\lambda$=75 nm×75 nm
Height: $0.436\lambda$=218 nm
Filling: resist
Background: BARC (90 nm) on Si
$\theta$, $\phi$: 8.13°, 45°
Polarization: parallel
where $\theta$ is the angle of incidence with respect to the z axis and $\phi$ is the azimuth angle for the incident radiation.

Figure 19:
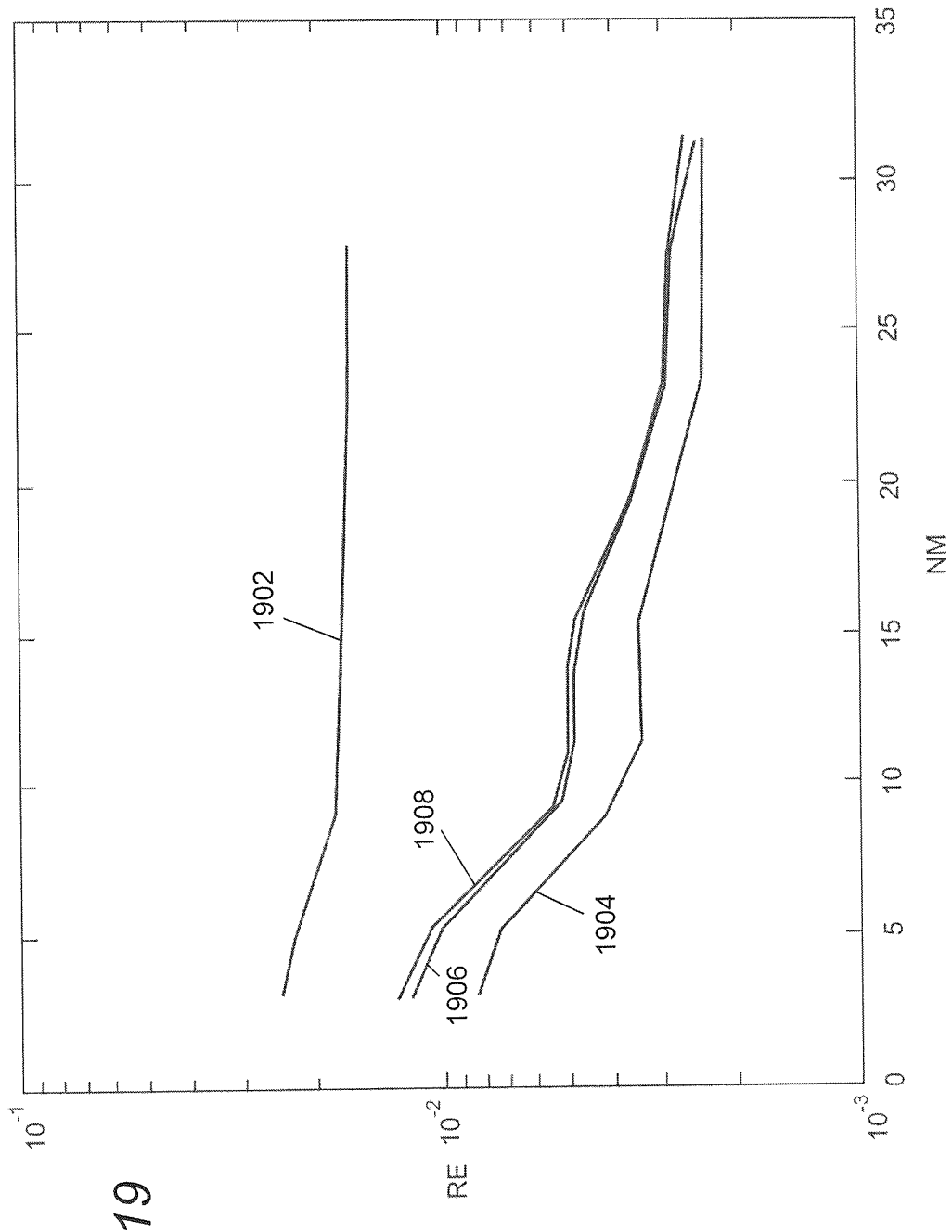
FIG. 19 depicts convergence results of the prior art VIM system, calculated using the prior art method described with reference to FIG. 11, compared with RCWA results.

FIG. 19 illustrates the convergence results of the prior art VIM system, calculated using the method described with reference to FIG. 11, versus the RCWA calculation. The vertical axis in FIG. 11 is the relative error, RE, given by $|R_p - R_p^*|/|R_p^*|$ where $R_p$ is the reflection coefficient for parallel polarization, where the electric field is parallel to the plane of incidence and $R_p^*$ is the converged solution of RCWA with sufficient modes to achieve a five digit accuracy. The horizontal axis is the number of modes, NM, which is the number of terms in the truncated Fourier series in one direction and using an identical number of modes the other direction. Several graphs are shown each corresponding to a different number of sample points in z. Graph 1902 is 2 sample points, graph 1904 is 4 sample points, graph 1906 is 8 sample points and graph 1908 is for 16 sample points. The graphs for 32, 164 and 128 sample points overlay the graph for 16 sample points 1908.

Typically 8 or 16 sample points in z are used for structures comprising resist in the simulation of lithographic process structures and 7 to 9 modes are used, corresponding to mode indices from −N to +N, where N=3 or 4. For higher contrast material such as metal or silicon a larger number of modes is needed to describe the fields properly.

The large relative errors for all graphs in FIG. 19 indicate poor convergence using the volume integral method and this is the effect of the concurrent jumps in permittivity and electric field as mentioned above. As discussed above, in the VIM system it is not practical to use the Li inverse rule to overcome the convergence problem because of the large number of matrix inverses that become computation limiting.

Figure 20:
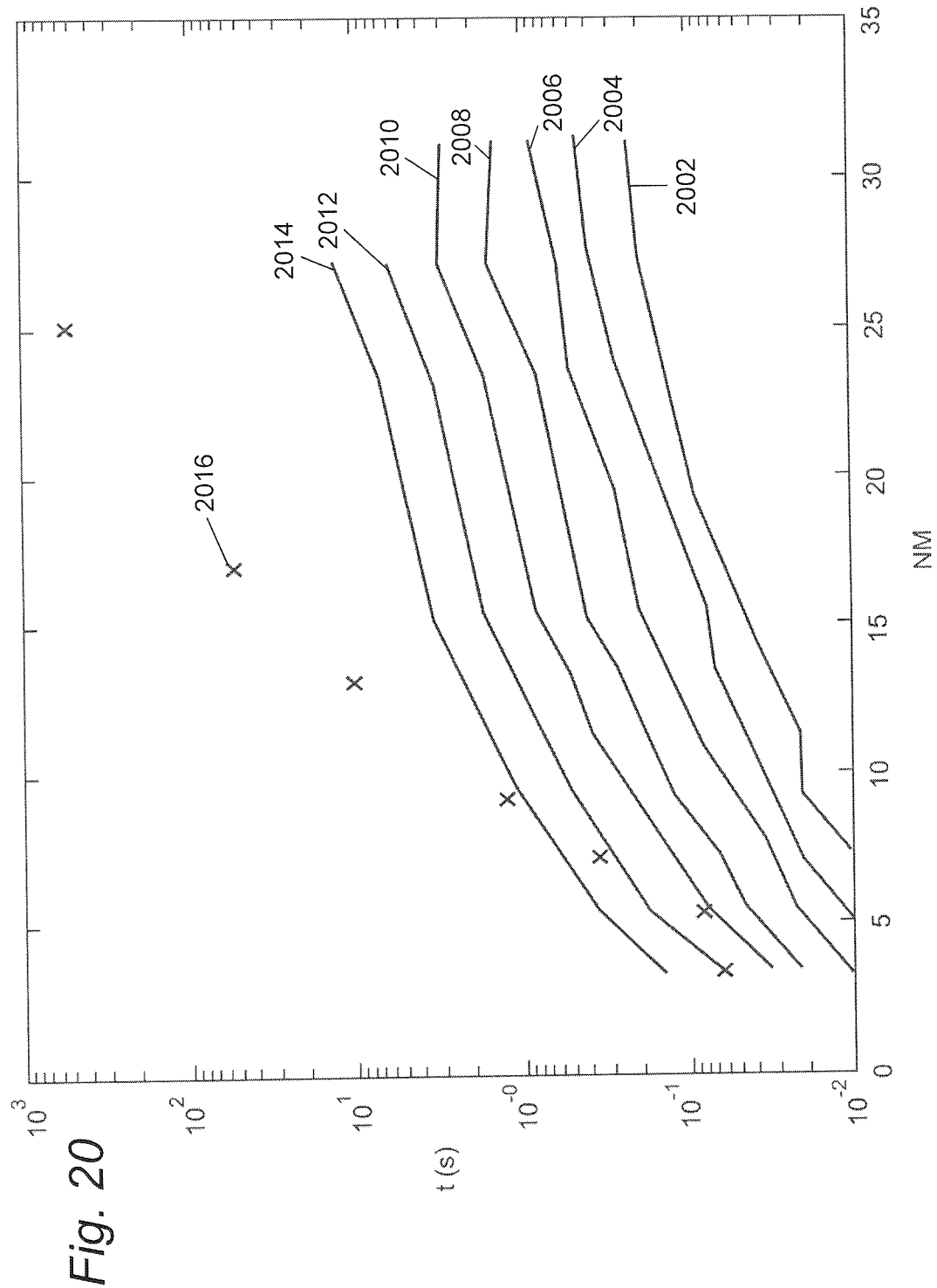
FIG. 20 depicts timing results produced from the same data as shown in FIG. 19.

FIG. 20 shows timing results with graphs derived from the same data as shown in FIG. 19 but with a vertical axis of CPU time, t, in seconds and a horizontal axis of the number of modes, NM. Graphs 2002 to 2014 are plots for 2, 4, 8, 16, 32, 64 and 128 sample points in z respectively. The x symbols 2016 are the results for RCWA calculations of the same structure.

Figure 21:
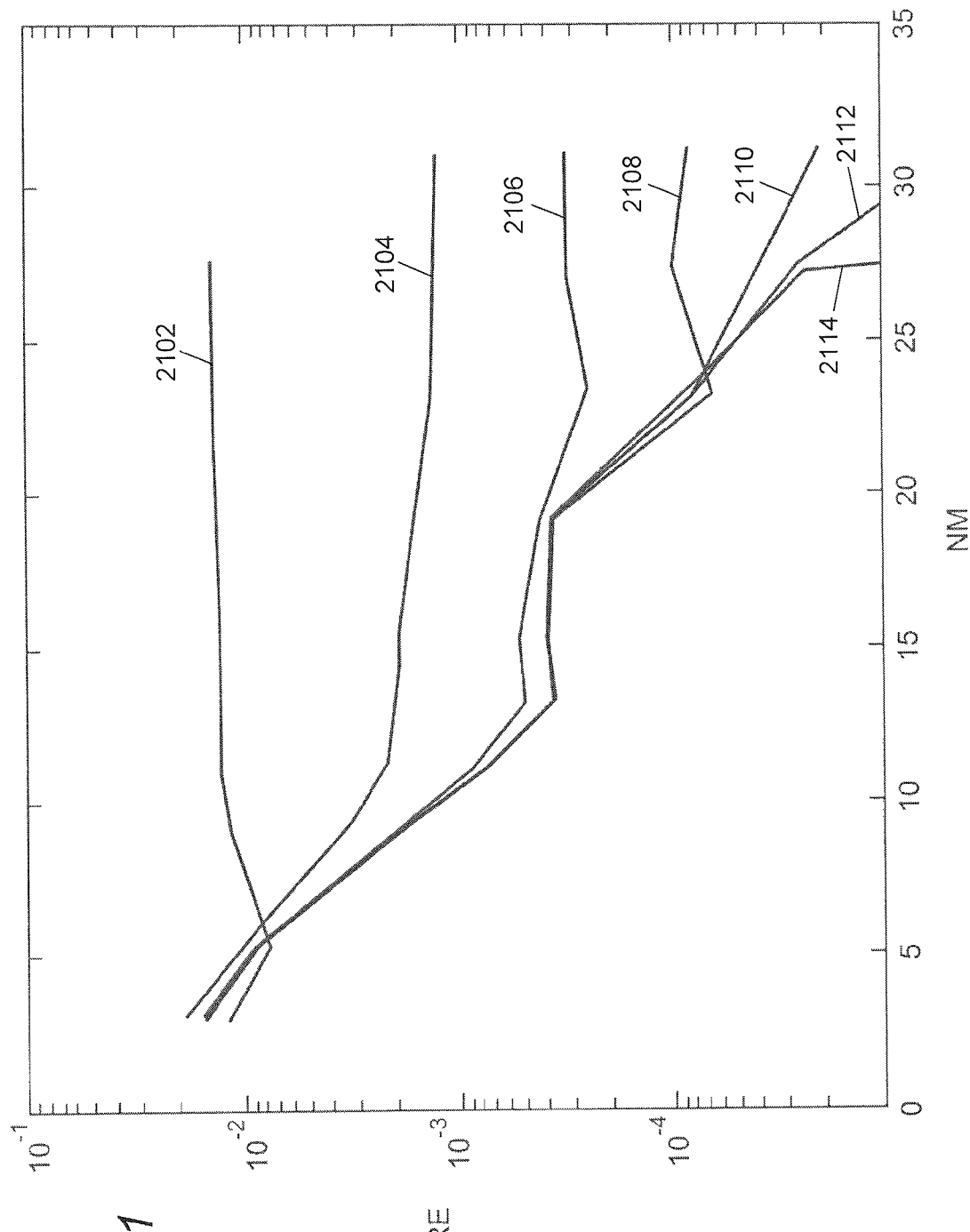
FIG. 21 depicts improved convergence results produced in accordance with an embodiment of the present invention, compared with RCWA results.

FIG. 21 shows greatly improved convergence in accordance with an embodiment of the present invention using the method discussed above in relation to FIGS. 12 and 13. The graphs in FIG. 21 should be compared with the graphs in FIG. 19 but noting that the vertical scale in FIG. 21 spans a larger range and shows over two orders of magnitude lower relative error than that shown in FIG. 19. Graphs 2102 to 2114 are plots for 2, 4, 8, 16, 32, 64 and 128 sample points in z respectively.

Figure 22:
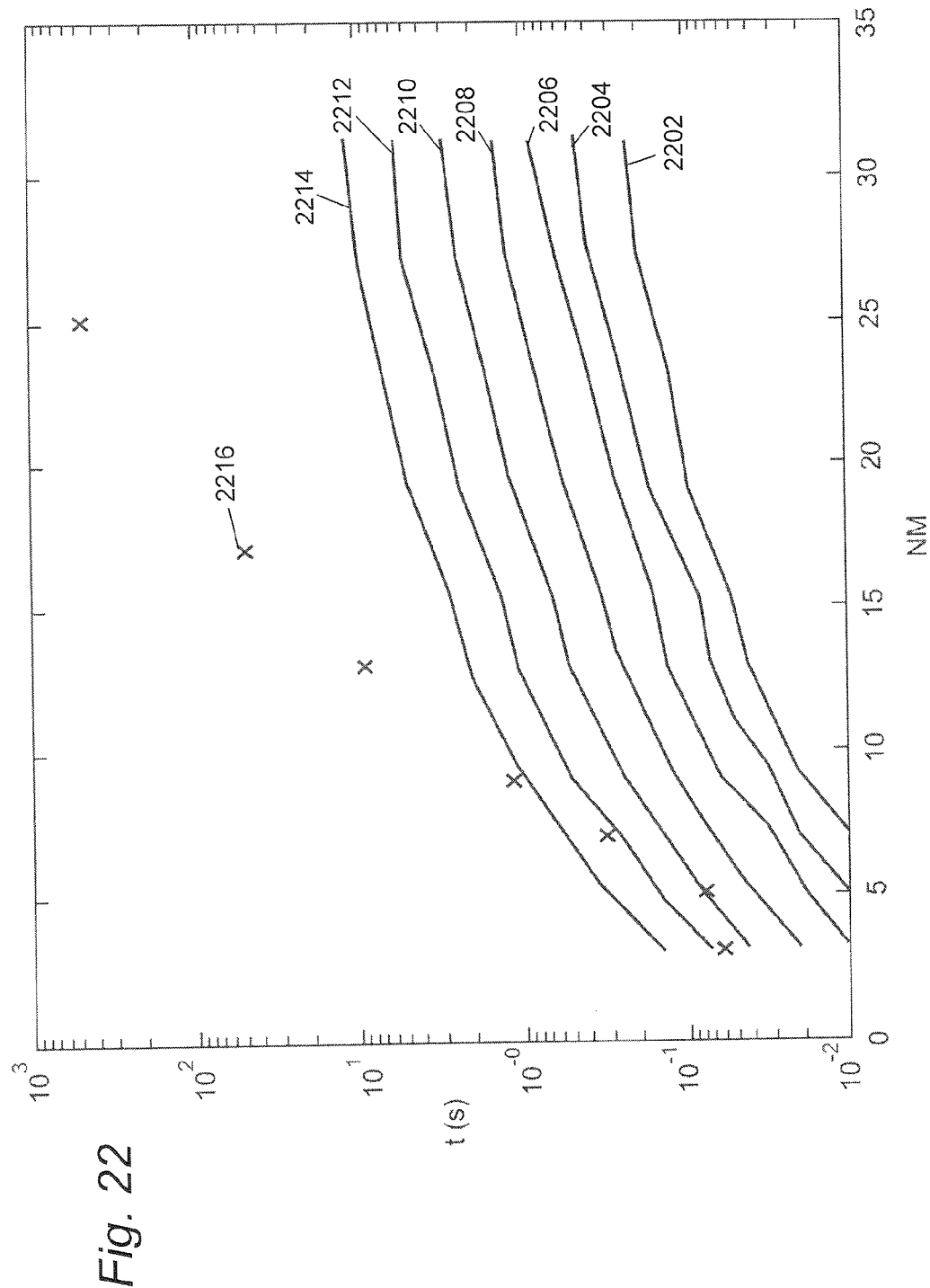
FIG. 22 depicts timing results produced in accordance with an embodiment of the present invention, compared with RCWA results.

FIG. 22 shows timing information on the same axes as FIG. 20 but for data generated in accordance with an embodiment of the present invention using the method discussed above in relation to FIGS. 12 and 13. Graphs 2202 to 2214 are plots for 2, 4, 8, 16, 32, 64 and 128 sample points in z respectively. The x symbols 2216 are the results for RCWA calculations of the same structure.

It can be seen that the CPU time, t, versus the number of modes, NM, is similar to that shown in FIG. 20.

FIGS. 21 and 22 therefore show clearly that the present invention greatly improves the convergence of the numerical solution using the volume integral method.

Embodiments of the present invention also require much less memory resources than RCWA. The RCWA storage requirement is $375*((M_1*M_2)^2)*$precision. The VIM storage requirement is approximately $60*(M_1*M_2*N)*$precision. Here, the number of modes in x is $M_1$, the number of modes in x is $M_2$ and the number of samples in z is N. A typical working point for VIM is $N \approx 4*(M_{1,2}/pitch_{x,y})*$height.

Table 1 show results obtained for memory usage:

TABLE 1

Memory Usage Comparison

| # modes/<br>dimension | RCWA<br>(estimated) | VIM<br>(measured) |
|---|---|---|
| 7 | 14 MB | 5.5 MB |
| 37 | 10 GB | 106 MB |
| 47 | 28 GB | 198 MB |

The following conditions were used for producing the data in Table 1:

pitchx=pitchy
M1=M2
height/pitch=0.436
Precision=complex double
VIM: operating at working point Table 1 clearly shows that the VIM has lower storage demands than RCWA for a typical grating.

Further embodiments will be described below.

Introduction

The volume integral equation method (VIM) consists of a set of two equations. The first one is the integral representation that describes the total electric field in terms of the incident field and contrast current density, where the latter interacts with the Green's function, viz $$e^i(m_1, m_2, z) = e(m_1, m_2, z) - \int_{z' \in \mathbb{R}} \overline{G}(m_1, m_2, z, z') j(m_1, m_2, z') dz', \quad (1.1)$$

for $m_1, m_2 \in \mathbb{Z}$. Further, $\overline{G}$ denotes the spectral Green's function of the background medium, which is planarly stratified in the z direction, $e(m_1, m_2, z)$ denotes a spectral component of total electric field $E(x,y,z)$, written in a spectral base in the xy plane, and $j(m_1, m_2, z)$ denotes a spectral component of the contrast current density $J^c(x,y,z)$, also written in a spectral base in the xy plane.

The second equation is a relation between the total electric field and the contrast current density, which is essentially a constitutive relation defined by the materials present in the configuration, viz $$J^c(x,y,z) = j\omega[\epsilon(x,y,z) - \epsilon_b(z)]E(x,y,z), \quad (1.2)$$

where $J^c$ denotes the contrast current density, $\omega$ is the angular frequency, $\epsilon(x,y,z)$ is the permittivity of the configuration, $\kappa_b(z)$ is the permittivity of the stratified background, and E denotes the total electric field, all written in a spatial basis. The transformation of the latter equation to a spectral basis in the xy plane is the main focus of the present document.

A straightforward approach is to transform Eq. (1.2) directly to the spectral domain, as proposed in [1,2], i.e., $$j(m_1, m_2, z) = \sum_{k=M_{1l}}^{M_{1h}} \sum_{l=M_{2l}}^{M_{2h}} \chi_s(m_1 - k, m_2 - l, z) e(k, l, z), \quad (1.3)$$

where $M_{1l}$ and $M_{2l}$ are the spectral lower bounds and $M_{1h}$ and $M_{2h}$ the spectral upper bounds that are taken into account for the finite Fourier representation of E and $J^c$. Further, $\chi_s(k,l,z)$ are the Fourier coefficients of the contrast function $x(x,y,z)$ with respect to the transverse (xy) plane. However, one of the major numerical issues in dealing with field-material interactions in a spectral basis is the observation that a simple product equation in real space is not always accurately reproduced by a convolution in Fourier space if one or both representations of the product variables have a finite (or truncated) Fourier expansion (as is the case in numerical implementations). In more detail, it has been shown that if both variables of the product show a so-called concurrent complementary jump condition, then the "inverse rule" has much better accuracy properties than the "Laurent rule", which is the standard convolution for the truncated Fourier expansions. This observation has been worked out by Li [3,4] in more detail for 2D and 3D field-material interactions within the context of RCWA.

Within VIM, these observations are equally relevant. Since we employ a spectral discretization of the electric field and the contrast current density, we are faced with a similar problem. Although the jumps in E and the contrast function are concurrent, they are not complementary, since the contrast function is zero outside the support of the perturbing geometry with respect to the background. Therefore, the rationale of Li's rules needs careful interpretation. Further, another major issue within VIM is the efficiency of the inverse rule. Whereas the Laurent rule has a low computational complexity owing to FFT implementations, the inverse rule typically leads to a full matrix-vector product, which seriously degrades the efficiency of VIM, as observed in [2] for approximated rules proposed by Lalanne [5]. Therefore, it is desirable to look for ways in which we can retain a convolution structure, without sacrificing the accuracy in a spectral base. To this end, we propose to formulate and solve a modified k-space Lippmann-Schwinger equation of the form $$e^i(m_1, m_2, z) = \quad (1.4)$$

$$(C_\epsilon F)(m_1, m_2, z) - \int_{z' \in \mathbb{R}} \overline{G}(m_1, m_2, z, z')(V_\epsilon F)(m_1, m_2, z') dz',$$

for $m_1, m_2 \in \mathbb{Z}$. Further, $\overline{G}$ denotes again the spectral Green's function of the background medium, and the operators $C_\epsilon$ and $V_\epsilon$ are operators that allow for an efficient matrix-vector product via 1D and/or 2D FFTs.

2 Investigation 2.1 Preliminaries

The relation between the total electric field and the contrast current density is derived from Maxwell's equations and the notion of a background configuration. The choice of the background is related to the ability of finding the Green's function for this background. Hence, typically, the background is a simplified configuration such as a planarly stratified medium. Here, we will assume that the stratification takes place in the z-direction and consists of materials with constant permeability through-out and therefore only variation in the permittivity. Looking at the Ampere-Maxwell equation, we have, in absence of primary sources, $$\nabla \cdot H = j\omega D = j\omega \epsilon E, \quad (2.1)$$

where H is the magnetic field strength, $\omega$ is the angular frequency, D is the electric flux density, s is the permittivity, and E is the electric field strength.

If we now indicate the permittivity of the background by $\epsilon_b$, then the contrast current density J is defined through the equation $$\nabla \times H = j\omega(\epsilon - \epsilon_b)E + j\omega \epsilon_b E = J + j\omega \epsilon_b E. \quad (2.2)$$

Further, we wish to define the normalized quantity q as $$q = \frac{1}{j\omega}(\epsilon_b)^{-1} J = (\epsilon_b)^{-1}(\epsilon - \epsilon_b)E = \chi E, \quad (2.3)$$

where $\chi$ is the contrast function. With this notion, we introduce the following $$\epsilon_{r,b} = (\epsilon_b)^{-1}\epsilon = I + \chi, \quad (2.4)$$

$$\hat{D} = (\epsilon_b)^{-1} D, \quad (2.5)$$

$$q = \hat{D} - E, \quad (2.6)$$

where I is the identity operator.

2.2 Rationale Behind the Inverse Rule

Let us consider a 1D periodic function $V(x)$, with period $p$, and its corresponding Fourier series with coefficients $v_n$, $n \in \mathbb{Z}$. Then the relation between them is given by $$V(x) = \sum_{n=-\infty}^{\infty} v_n \exp\left(-j\frac{2\pi n x}{p}\right), \tag{2.7}$$

$$v_n = \frac{1}{p} \int_{-p/2}^{p/2} V(x) \exp\left(j\frac{2\pi n x}{p}\right) dx. \tag{2.8}$$

Further, we introduce a 1D periodic function $K(x)$, also with period $p$, and its corresponding Fourier coefficients $k_n$.

We are interested in approximating the product $K(x)V(x)$ in terms of the Fourier coefficients $k_n$ and $v_n$. If $K(x)$ and $V(x)$ are continuous periodic functions, then Fourier theory tells us that $$K(x)V(x) = \sum_{n=-\infty}^{\infty} c_n \exp\left(-j\frac{2\pi n x}{p}\right), \tag{2.9}$$

where $$c_n = \sum_{l=-\infty}^{\infty} k_{n-l} v_l, \tag{2.10}$$

where the series converges in norm, owing to the continuity of $K$ and $V$. This rule is known as the Laurent rule or the convolution rule. Further, if we are interested in an approximation of $K(x)V(x)$ in a finite (or truncated) Fourier series (as in all numerical implementations), which we indicate by a tilde, e.g., $$V(x) \approx \tilde{V}(x) = \sum_{n=-N}^{N} v_n \exp\left(-j\frac{2\pi n x}{p}\right), \tag{2.11}$$

then the question arises if we can build a converging approximation of $K(x)V(x)$ in a finite Fourier series, from the finite Fourier series $\tilde{V}(x)$. Hence, can we construct coefficients $c_n$, such that $$K(x)V(x) \approx \tilde{K}\tilde{V}(x) = \sum_{n=-N}^{N} c_n \exp\left(-j\frac{2\pi n x}{p}\right), \tag{2.12}$$

where $$c_n = \sum_{l=-N}^{N} k_{n-l} v_l. \tag{2.13}$$

Note that the coefficients of the finite Fourier series of $\tilde{V}(x)$ are restricted to the set $\{-N, \ldots, N\}$, whereas the coefficients of $\tilde{K}(x)$ are needed on the set $\{-2N, \ldots, 2N\}$. This is the case in many convolution problems, where $V$ represents a signal that needs to be transformed by a filter with a prescribed convolution kernel $K$. This finite Laurent rule can be implemented via a matrix-vector product, where the coefficients $k_n$ are arranged in a matrix and the coefficients $v_n$ are organized as a column vector. If the coefficients of $v_n$ are organized according to their index $n$, then the matrix with the coefficients $k_n$ is a Toeplitz matrix. This Toeplitz matrix allows for an efficient matrix-vector product via forward and backward Fast-Fourier Transforms (FFTs).

The papers by Li [3,4] demonstrate that the finite Laurent rule in Eq. (2.13) can be applied if the function $V(x)$ and/or the function $K(x)$ is continuous everywhere. Further, if $V(x)$ is discontinuous at a finite number of points in a period and $K(x)$ is continuous in the vicinity of these points, then the finite Laurent rule also applies. In such a situation we say that $V(x)$ and $K(x)$ are Fourier factorizable. However, when there are points at which $V(x)$ and $K(x)$ are both discontinuous, i.e., the functions $V(x)$ and $K(x)$ have so-called concurrent jumps, then the finite Laurent rule has poor approximation properties.

For one special case, Li has shown that there is another rule, known as the inverse rule, that leads to better approximation properties. This special case revolves around the situation in which $K(x)$ and $V(x)$ have discontinuities at the same points but their discontinuities are complementary, i.e., the discontinuities in $K(x)$ and $V(x)$ are such that the product of $K(x)$ and $V(x)$ is continuous. To construct a rule, we notice that the function $W(x)=K(x)V(x)$. Then, the Laurent rule applied to $W(x)$ and the kernel $1/K(x)$ leads to the coefficients of $V(x)$, i.e., $$V(x) = \frac{1}{K(x)} W(x) = \sum_{n=-\infty}^{\infty} \left[\sum_{l=-\infty}^{\infty} \kappa_{n-l} w_l\right] \exp\left(-j\frac{2\pi n x}{p}\right), \tag{2.14}$$

where $\kappa_n$ are the coefficients of the Fourier series of $1/K(x)$ and $w_n$ are the coefficients of the Fourier series of $W(x)$. Owing to the continuity of $W(x)$, the finite Laurent rule can be applied to get a finite Fourier series approximation of $W(x)/K(x)$, which leads to a Toeplitz matrix $T$ for the coefficients $\kappa_n$ and a vector with coefficients $w_n$, such that $$v = \begin{pmatrix} v_{-N} \\ \vdots \\ v_N \end{pmatrix} = T \begin{pmatrix} w_{-N} \\ \vdots \\ w_N \end{pmatrix} = Tw. \tag{2.15}$$

Hence $W(x)$ and $1/K(x)$ are Fourier factorizable. Finally, we invert the matrix $T$ to arrive at $$w = T^{-1} v, \tag{2.16}$$

hence the name "inverse rule".

2.3 Modified Li Rules for a Single Brick with Edges Aligned Along the Axes of the 2D-Periodic Unit Cell Let us consider a configuration for which the background medium at a fixed $z$ position is constant and the contrast function a non-zero continuous function, e.g., a constant, on a rectangular domain within a rectangular unit cell of a periodic configuration in the xy plane. Further, we assume that the rectangular domain has the same orientation as the unit cell. To define the shape of the support of $\chi$, we introduce $$\prod_{\Delta}(x) = \begin{cases} 1 & x \in [-\Delta/2, \Delta/2] \\ 0 & \text{elsewhere,} \end{cases} \tag{2.17}$$

At a fixed position along the z direction, we can now define the permittivity with respect to the background and its inverse as (assuming that the materials are isotropic, i.e., the permittivity is a scalar)

$$\epsilon_{r,b} = 1 + \chi_c \prod_{\Delta x}(x-x_0) \prod_{\Delta y}(y-y_0), \tag{2.18}$$

$$\epsilon_{r,b}^{-1} = 1 + \hat{\chi}_c \prod_{\Delta x}(x-x_0) \prod_{\Delta y}(y-y_0), \tag{2.19}$$

where $\chi_c$ is a continuous function or a constant, $(x_0, y_0)$ is the center position of the rectangular support, and $$\hat{\chi}_c = -\frac{\chi_c}{1+\chi_c}, \quad (2.20)$$

which follows from the condition $\epsilon_{r,b} \cdot \epsilon_{r,b}^{-1} 1$.

We now introduce the convolution operators $\tilde{P}_x$ and $\tilde{P}_y$ in finite Fourier space, acting on an arbitrary field v (in a spectral base), as $$(\tilde{P}_x v)(m_1, m_2) = \sum_{m_1'=-M_{1l}}^{M_{1h}} \tilde{\Pi}_{\Delta x}(m_1 - m_1') v(m_1', m_2), \quad (2.21)$$

$$(\tilde{P}_y v)(m_1, m_2) = \sum_{m_2'=-M_{2l}}^{M_{2h}} \tilde{\Pi}_{\Delta y}(m_2 - m_2') v(m_1, m_2'), \quad (2.22)$$

for $m_1 \in \{-M_{1b}, \ldots, M_{1h}\}$ and $m_2 \in \{-M_{2b}, \ldots, M_{2h}\}$, which are the integer indices of the 2D Fourier coefficients. Further, we have $$\tilde{\Pi}_{\Delta x}(m_1) = \frac{1}{a} \int_{-a/2}^{a/2} \Pi_{\Delta x}(x - x_0) \exp\left(-j \frac{2\pi m_1 x}{a}\right) dx, \quad (2.23)$$

$$\tilde{\Pi}_{\Delta y}(m_2) = \frac{1}{b} \int_{-b/2}^{b/2} \Pi_{\Delta y}(y - y_0) \exp\left(-j \frac{2\pi m_2 y}{b}\right) dy, \quad (2.24)$$

where a and b are the dimensions of the unit cell in the x and y direction, respectively, and we assume that the support of the pulse functions in the x and y direction lie within the integration intervals.

In the spatial domain, we have the following relation between the x-components of the normalized electric flux and the electric field $$\hat{D}_x = [1 + \hat{\chi}_c \Pi_{\Delta x}(x-x_0) \Pi_{\Delta y}(y-y_0)] E_x, \quad (2.25)$$

which would directly lead to its spectral counterpart $$\tilde{\hat{D}}_x = (I + \hat{\chi}_c \tilde{P}_x \tilde{P}_y) E_x, \quad (2.26)$$

where I represents the identity operator and the ~ on $E_x$ and $\hat{D}_x$ denotes a finite Fourier representation. However, this formula completely ignores the fact that the permittivity function and the electric field have concurrent jumps, which severely degrades the performance of this approximation. Therefore, we will now follow Li's line of reasoning [3,4] to arrive at a combination of Laurent and inverse rules.

Starting from the Relation $$E_x = [1 + \hat{\chi}_c \Pi_{\Delta x}(x-x_0) \Pi_{\Delta y}(y-y_0)] \hat{D}_x, \quad (2.27)$$

we notice that $\hat{D}_x$ is continuous in the x direction and therefore the multiplication by $\Pi_{\Delta x}$ can be replaced in the spectral domain by the operator $\tilde{P}_x$. However, in the y direction, we observe concurrent jumps in the above formula. Since the pulse function $\Pi_{\Delta y}$ is a spatial projection operator, we can construct in inverse owing to the idempotency property and the fact that $\tilde{P}_x$ acts only as a constant multiplier in the y-direction and commutes with $\Pi_{\Delta y}$. For such a case, the inverse of $I + A\Pi_{\Delta y}$ is of the form $I + B\Pi_{\Delta y}$, where B follows from the algebraic property $$(I + B\Pi_{\Delta y})(I + A\Pi_{\Delta y}) = I + (B + A + BA)\Pi_{\Delta y}, \quad (2.28)$$

from which it follows that $(B+A+BA)=0$, i.e., $B = -A(I+A)^{-1}$. Further, we denote the spatial representation of the finite spectral representation of $\tilde{P}_x \tilde{\hat{D}}_x$ as $P_x \hat{D}_x$ and similar notations for $P_y$. With these notations and following the above line of reasoning, we arrive at $$[I - \hat{\chi}_c P_x (I + \hat{\chi}_c P_x)^{-1} \Pi_{\Delta y}] E_x = \hat{D}_x. \quad (2.29)$$

At this point, the multiplication operator $\Pi_{\Delta y}$ has a spectral counter part in terms of the finite Laurent rule, which we denote by Py. Further, owing to the fact that $P_x$ and $P_y$ act on different indices, the operator $(I + \hat{\chi}_c P_x)^{-1}$ commutes with $P_y$.

This brings us to the following relation between the normalized electric flux and the electric field, both expressed in terms of a finite Fourier series.

$$\hat{D}_x = [I - \hat{\chi}_c P_x P_y (I + \hat{\chi}_c P_x)^{-1}] E_x, \quad (2.30)$$

$$\hat{D}_y = [I - \hat{\chi}_c P_x P_y (I + \hat{\chi}_c P_y)^{-1}] E_y, \quad (2.31)$$

$$\hat{D}_z = (I + \chi_c P_x P_y) E_z, \quad (2.32)$$

where the z component follows owing to the observation that $E_z$ is continuous in the xy plane. For the volume integral equation, we are only interested in the total electric field E and the normalized contrast current density q. For the latter we have $$q_x = \hat{D}_x - E_x = \chi_c P_x P_y \left[\frac{1}{1+\chi_c}(I + \hat{\chi}_c P_x)^{-1}\right] E_x, \quad (2.33)$$

$$q_y = \hat{D}_y - E_y = \chi_c P_x P_y \left[\frac{1}{1+\chi_c}(I + \hat{\chi}_c P_y)^{-1}\right] E_y, \quad (2.34)$$

$$q_z = \hat{D}_z - E_z = \chi_c P_x P_y E_z, \quad (2.35)$$

where we have employed the relation between $\hat{\chi}_c$ and $\chi c$.

The presence of the inverse operators $(I + \hat{\chi}_c P_x)^{-1}$ and $(I + \hat{\chi}_c P_y)^{-1}$ in the above matrix-vector product, to obtain q from E, leads to a serious increase in the numerical complexity of the matrix-vector product of the overall volume integral equations. Therefore, it is highly desirable to avoid these inverses, without sacrificing the increased accuracy that they bring. Therefore, we propose to introduce a new vector field F that has the following relation to E.

$$E_x = (1+\chi_c)(I + \hat{\chi}_c P_x) F_x, \quad (2.36)$$

$$E_y = (1+\chi_c)(I + \hat{\chi}_c P_y) F_y, \quad (2.37)$$

$$E_z = F_z, \quad (2.38)$$

which can be implemented via 1D FFTs along the x direction for the first equation and along the y direction for the second equation.

Then, the relation between q and F becomes $$q = \chi_c P_x P_y F, \quad (2.39)$$

which can be implemented via 2D FFTs in the xy-plane.

Now both the relation between E and F and the relation between q and F have convolution operators according to the finite Laurent rule, which makes their matrix-vector products efficient, since they can be implemented by (a combination of) 1D and 2D FFTs. Hence we solve the volume integral equation for the vector field F instead of E and via an additional post-processing step we obtain the electric field E from Eqs (2.36) to (2.38). The change in this procedure compared to the prior art procedure is that we now use two operations (i.e., one for E and one for q) instead of one (only for q), and a post processing step. However, these two operations in the new procedure according to embodiments of the present invention have a much more efficient implementation that the single one in the prior art procedure.

2.4 Normal-Vector Field Formulation

The discussion of the modified Li rules above shows that the low computational complexity via FFTs is rather strict on the type of geometry of the contrast function. Therefore, it is of prime importance to find a framework in which FFTs remain the dominant operation of the field-material interaction equations. We find a suitable starting point in the paper [6]. One of the ideas put forward there, is the introduction of an auxiliary vector field, which is continuous everywhere, with the possible exception of isolated points or lines that correspond to edges and corners in the geometry of the permittivity function. This is similar to the situation in the preceding section, in which we also introduced an (other) intermediate continuous vector field F, which allowed for convolutions with good convergence in the form of the finite Laurent rule. However, a significant difference is that [6] does not teach using the auxiliary vector field for solving the linear system, instead [6] teaches using E as the basis for solving the linear system.

It is possible to set up a set of equations that relate the contrast current density J (or q) and the electric field E on the one hand to the continuous vector field F, in the form of convolutions in the spectral domain. Since F is continuous, convolutions operating on it take the form of the finite Laurent rule and can therefore be executed by means of FFTs. In that way, we arrive at a set of equations in which F is the fundamental unknown for which we solve the system and by an additional post processing step we obtain the electric field and/or the contrast current density, from which we can derive the desired scattering properties of the configuration e.g., the reflection coefficients.

From the preliminary discussion, the relation between F and J follows from the relation between E and D on the one hand and F on the other. In the notation of [6], the idea is to establish the relations $$E = C_\epsilon F, \quad (2.40)$$

$$D = \epsilon C_\epsilon F. \quad (2.41)$$

The vector field F is constructed from a combination of field components of the electric field and components of the electric flux density. From the boundary conditions at a material interface, we know that the tangential components of the electric field and the normal components of the electric flux density are continuous, with the possible exception of points and lines that correspond to corners and edges of the material interfaces. To filter out these continuous components of E and D, a real-valued normal-vector field is introduced. This normal-vector field $n(x,y,z)$ has the following properties:

It is pointing orthogonal to every material interface.

It has unit length at every point in space.

Apart from these, there are no other restrictions to define this vector field, although it is convenient to include other properties, such as some form of continuity.

The vector field n can be used to filter out the discontinuous component of the electric flux density that results in the continuous scalar field $D_n = (n,D)$, where (.,.) denotes the scalar product. Further, from the normal-vector field, we can find two so-called tangential-vector fields $t_1$ and $t_2$, which together with n form an orthonormal basis at every point in the 3D space. For example, let $n_x$ and $n_y$ be the x and y components of the normal-vector field $t_1$ can be constructed as $$t_1 = -n_y u_x + n_x u_y, \quad (2.42)$$

where $u_x$ and $u_y$ denote the unit vectors along the x and y direction, respectively. Finally, the vector field $t_2$ is generated via the cross product between n and $t_1$.

The tangential-vector fields can be used to extract the continuous components of the electric field as $$E_T = (E, t_1) t_1 + (E, t_2) t_2. \quad (2.43)$$

Following [6], we now construct the continuous vector field F as $$F = E_T + D_n n = (E, t_1) t_1 + (E, t_2) t_2 + (n, D) n = F_{t_1} t_1 + F_{t_2} t_2 + F_n n. \quad (2.44)$$

The normal-vector field n gives rise to the definition of the operator $P_n$ as $$P_n v = (n, v) n, \quad (2.45)$$

where v is an arbitrary 3D vector field. From the properties of the normal-vector field n, we observe that $P_n$ is a projection operator and therefore it is idempotent, i.e., $P_n P_n = P_n$. Similarly, we can introduce the operator $P_T$ as $$P_T v = (v, t_1) t_1 + (v, t_2) t_2, \quad (2.46)$$

which is also a projection operator. We will now show how these operators Pn and PT can be used to construct the operators in Eq. (2.40) from the vector field F.

We start from the spatial-domain relations between the electric field and electric flux density on the one hand and the definition of the vector field F on the other. We have $$D = M_\epsilon E, \quad (2.47)$$

$$E = M_\epsilon^{-1} D, \quad (2.48)$$

$$F = P_T E + P_n D, \quad (2.49)$$

where $M_\epsilon$ is the multiplication operator that multiplies by the, generally anisotropic, permittivity tensor $\epsilon$ and $M_\epsilon^{-1}$ is the multiplication operator that multiplies by the (point-wise) inverse of the permittivity function.

First, we establish a relation between E and F. Since we have $$E = P_n E + P_T E, \quad (2.50)$$

$$P_T F = P_T E, \quad (2.51)$$

$$P_n F = P_n M_\epsilon E = (P_n M_\epsilon P_n) E + (P_n M_\epsilon P_T) E = (P_n M_\epsilon P_n) E + (P_n M_\epsilon P_T) F \quad (2.52)$$

After rearranging the latter equation and employing the idempotency of $P_n$, we obtain $$(P_n M_\epsilon P_n) P_n E = (P_n - P_n M_\epsilon P_T) F. \quad (2.53)$$

We now observe that in the above equation both sides of the equation belong to the range of the operator $P_n$. One important property of projection operators is that projection operators are uniquely identified with the identity operator on their range, owing to their idempotency. Therefore, if we restrict the left-hand side as a mapping from the range of $P_n$ to the range of $P_n$, which is possible since $P_n$ appears on both sides of the operator that works on E, we can invert the operator on the left-hand side to arrive at $$P_n E = (P_n M_\epsilon P_n)^{-1} (P_n - P_n M_\epsilon P_T) F, \quad (2.54)$$

where $(P_n M_\epsilon P_n)^{-1}$ is the inverse of $(P_n M_\epsilon P_n)$ on the range of $P_n$, i.e., $(P_n M_\epsilon P_n)^{-1} (P_n M_\epsilon P_n) = P_n$. The existence of the inverse operator will be established below.

Hence, the linear operator $C_\epsilon$ in Eq. (2.40) is given by $$E = C_\epsilon F = [P_T + (P_n M_\epsilon P_n)^{-1} (P_n - P_n M_\epsilon P_T)] F. \quad (2.55)$$

In a similar way, we can derive a relation between the electric flux density and the vector field F:

$$D = P_n D + P_T D = P_n F + P_T D, \quad (2.56)$$

$$P_T D = P_T M_\epsilon E = P_T M_\epsilon P_T E + P_T M_\epsilon P_n E = P_T M_\epsilon P_T F + P_T M_\epsilon P_n E. \quad (2.57)$$

In the second equation, we can now employ Eq. (2.54) to eliminate E, i.e., $$P_T D = P_T M_\epsilon P_T F + P_T M_\epsilon (P_n M_\epsilon P_n)^{-1} (P_n - P_n M_\epsilon P_T) F. \quad (2.58)$$

Hence, $$D = \epsilon C_\epsilon F = P_n + P_T M_\epsilon P_T + P_T M_\epsilon (P_n M_\epsilon P_n)^{-1} (P_n - P_n M_\epsilon P_T)] F = [P_n + P_T M_\epsilon C_\epsilon] F. \quad (2.59)$$

At this point, it is important to realize that all operators, with the possible exception of $(P_n M_\epsilon P_n)^{-1}$, i.e., $P_n$, $P_T$, and ME are point-wise multiplication operators in the spatial domain. Further, jumps in the permittivity profile, do not occur at the same position as (possible) jumps in the normal-vector field. However, in a product in which more than one projection operator (i.e., $P_n$ and/or $P_T$) or more than one material operator (e.g., $C_\epsilon$ and $M_\epsilon$) is involved, it is possible that concurrent jumps will occur. Further, the spatial idempotency properties of the projection operators are not maintained in a finite Fourier series expansion. Therefore, all idempotency properties are worked out in the spatial domain, before the operators are constructed in the Fourier domain. The simplest way to accomplish this, is to realize that each combination (product) of multiplication operators is again a multiplication operator. Therefore, we aim to construct a single multiplication operator for each term in the total operator $C_\epsilon$ and the operator $\epsilon C_\epsilon$. Once we have accomplished this, each multiplication operator in the spatial domain becomes a convolution operator in the spectral domain, which can be implemented by the finite Laurent rule since they all operate on the continuous vector field F.

2.4.1 The Operator $(P_n M_\epsilon P_n)^{-1}$

We now turn our attention to the operator $(P_n M_\epsilon P_n)^{-1}$. We will show that it is a point-wise multiplication operator and we will derive an expression for it.

From the definition of the projection operator Pn, we can readily derive $$P_n M_\epsilon P_n v = n(n,\epsilon n)(n,v) = (n,\epsilon n) P_n v = P_n (n,\epsilon n) v, \quad (2.60)$$

owing to the fact that (n,∈n) is a scalar field, which is never zero owing to the energy properties of the permittivity function, i.e., $(E, \epsilon^* E^*)$ for all possible electric fields E is a power density. Therefore, the inverse of the scalar field is simply given by $(n,\epsilon n)^{-1} = 1/(n,\epsilon n) = \xi$. Hence, $$(P_n M_\epsilon P_n)^{-1} = \xi P_n = M_\xi P_n = P_n M_\xi = P_n M_\xi P_n. \quad (2.61)$$

2.4.2 Normal-Vector Field Formulation for the Isotropic Case

In the case of isotropic media, the operator Ms is a scalar multiplication, owing to which the operators $P_n$ and $P_T$ on the one hand and Ms on the other hand commute. Further, the operator $(P_n M_\epsilon P_n)^{-1} = P_n M_{1/\epsilon} = M_{1/\epsilon} P_n$, where $M_{1/\epsilon}$ is the multiplication by the (scalar) inverse of E. From these observations, the operator $C_\epsilon$ becomes $$C_\epsilon = P_T + P_n M_{1/\epsilon}. \quad (2.62)$$

Further, the operator $\epsilon C_\epsilon$ becomes $$\epsilon C_\epsilon = P_T M_\epsilon + P_n. \quad (2.63)$$

2.4.3 Normal-Vector Field Formulation for a Binary Grating

A binary grating is a grating that has uniform cross-section over its entire height.

Assuming that z is the direction of the medium stratification and that the grating is defined in the interval $z \in [z_l, z_h]$, then within the latter interval the permittivity function of the grating structure is a function of x and y only, see FIG. 15. If we use a spatial discretization in z or a spectral one that is dedicated to the interval $z \in [z_l, z_h]$, then we can choose one of the tangential-vector fields parallel to the unit vector along the z direction throughout. The normal-vector field and the second tangential vector-field are then essentially two-dimensional vector fields, i.e., they are perpendicular to the z direction and depend only on the x and y coordinates. Once the normal-vector field has been determined, the second tangential vector-field follows from the cross product between the normal-vector field and the unit vector in the z direction. Hence, the problem of generating normal and tangential vector fields is reduced to generating only a normal-vector field. Further, the computation of the field-material interaction takes the form of a 2D convolution in the xy plane, which is decoupled with respect to the z direction. The normal-vector field can be generated in many ways. Suggestions are given in [7,8] within the context of RCWA.

2.4.4 Example: Coefficients of the Field-Material Interaction Matrix for an Isotropic Binary Grating Let us consider a rectangular unit cell $x \in [-a/2, a/2]$, $y \in [-b/2, b/2]$. For the interval $z \in [z_0, z_1]$ the permittivity function is given by s(x,y). Further, let $n_x(x,y)$ and $n_y(x,y)$ be the x and y components of the normal-vector field, $t_{1,x}(x,y) = -n_y(x,y)$, $t_{1,y}(x,y) n_x(x,y)$, and $t_2 = u_z$. For this case, with reference to Eq. (2.62), we have the operator equation $$\begin{pmatrix} E_x \\ E_y \\ E_z \end{pmatrix} = C_\varepsilon F = \begin{pmatrix} C_{xn} & C_{xt_1} & 0 \\ C_{yn} & C_{yt_1} & 0 \\ 0 & 0 & I \end{pmatrix} \begin{pmatrix} F_n \\ F_{t_1} \\ F_{t_2} \end{pmatrix}, \quad (2.64)$$

where the coefficients of the convolution operators C . . . are given by $$C_{xn}(m_1, m_2) = \frac{1}{ab} \int_{-a/2}^{a/2} \int_{-b/2}^{b/2} \frac{n_x(x,y)}{\varepsilon(x,y)} \exp\left[j\left(\frac{2\pi m_1 x}{a} + \frac{2\pi m_2 y}{b}\right)\right] dy\, dx, \quad (2.65)$$

$$C_{yn}(m_1, m_2) = \frac{1}{ab} \int_{-a/2}^{a/2} \int_{-b/2}^{b/2} \frac{n_y(x,y)}{\varepsilon(x,y)} \exp\left[j\left(\frac{2\pi m_1 x}{a} + \frac{2\pi m_2 y}{b}\right)\right] dy\, dx, \quad (2.66)$$

$$C_{xt_1}(m_1, m_2) = \frac{1}{ab} \int_{-a/2}^{a/2} \int_{-b/2}^{b/2} -n_y(x,y) \exp\left[j\left(\frac{2\pi m_1 x}{a} + \frac{2\pi m_2 y}{b}\right)\right] dy\, dx, \quad (2.67)$$

$$C_{xt_1}(m_1, m_2) = \frac{1}{ab} \int_{-a/2}^{a/2} \int_{-b/2}^{b/2} n_x(x,y) \exp\left[j\left(\frac{2\pi m_1 x}{a} + \frac{2\pi m_2 y}{b}\right)\right] dy\, dx. \quad (2.68)$$

and I represents the identity operator.

2.4.5 Normal-Vector Field Formulation for a Staircased Grating

A grating structure can be geometrically approximated by a staircase approximation in the direction of the stratification, i.e., the z direction, see FIG. 16. This means that we choose a sequence of disjoint intervals (slices) in the z direction and for each of these intervals we approximate the permittivity function by a permittivity function that is independent of the z direction. Then, by using a discretization that is dedicated to each of the intervals, we arrive at a sequence of binary gratings, for which we can apply the procedure indicated above in Section 2.4.3, i.e., we generate a normal-vector field for each slice and build a field-material interaction operator for each slice, which are both essentially two-dimensional.

2.5 Alternatives for the Modified Li Rules and Normal-Vector-Field Formulation that Maintain a Convolution Structure In the preceding sections, we have modified the so-called k-space Lippmann-Schwinger equations to construct an efficient matrix-vector product for the field-material interactions while retaining its accuracy in a spectral base. This was achieved by introducing an auxiliary vector field F that has a one-to-one correspondence to the electric field denoted by E, such that when F has been computed then E is obtained with very little additional computations. In essence, we have derived a set of equations of the form $$E^i = E - GJ, \tag{2.69}$$

$$E = C_\epsilon F, \tag{2.70}$$

$$J = j\omega(\epsilon C_\epsilon - \epsilon_b \cdot C_\epsilon)F, \tag{2.71}$$

where $E^i$ denotes the incident field, G denotes the matrix representation of the Green's function of the stratified background medium, and $C_\epsilon$ and $(\epsilon C_\epsilon)$ correspond to efficient matrix-vector products in the form of FFTs.

In the above case, the one-to-one correspondence between F and E allows for a compact and efficient formalism. However, other routes exist to achieve the goal of high accuracy together with efficient matrix-vector products. It is the aim of the present section to further explore and document these alternatives. The existing formalism can be extended by dropping the one-to-one correspondence between E and the auxiliary vector field F. This is for example the case when we introduce more degrees of freedom in the auxiliary vector field F than there are in the electric field E, as we will e.g., show in Section 2.5.2. Without further measures, the resulting set of linear equations for the vector field F will then be underdetermined and hence F is not unique, which is typically undesirable when iterative solvers are used, since it will typically lead to a large number of iterations or breakdown of the iterative process. To overcome this situation, we allow for an additional set of linear constraints between the quantities F, E, and/or J. With this rationale, we arrive at the following generalized set of modified Lippmann-Schwinger equations $$\begin{pmatrix} I & -G & 0 \\ C_{11} & C_{12} & C_{13} \\ C_{21} & C_{22} & C_{23} \\ C_{31} & C_{32} & C_{33} \end{pmatrix} \begin{pmatrix} E \\ J \\ F \end{pmatrix} = \begin{pmatrix} E^i \\ 0 \\ 0 \\ 0 \end{pmatrix}. \tag{2.72}$$

where each of the operators in the matrix equation above allows for an efficient matrix-vector product implementation, e.g., by means of FFTs.

2.5.1 Rules by Lalanne

Prior to the rules derived by Li for periodic structures with 2D periodicity, Lalanne [5] proposed a weighted-average formula for the permittivity matrix $M_\epsilon$ (denoted in [5] as E) and the inverse matrix of the inverse-permittivity matrix $(M_{inv(\epsilon)})^{-1}$ (denoted in [5] as $P^{-1}$). For this way of working, we can work with the combination of the electric field E and an auxiliary vector field F. The latter vector field is introduced at points where we encounter the product between $(M_{inv(\epsilon)})^{-1}$ and E, to achieve a fast matrix-vector product to compute the contrast current density J or its scaled counterpart q.

$$J = j\omega\{[\alpha M_\epsilon + (1-\alpha)(M_{inv(\epsilon)})^{-1}]E - \epsilon_b E\} = j\omega[\alpha(M_\epsilon - \epsilon_b I)E + (1-\alpha)F], \tag{2.73}$$

where F satisfies $$M_{inv(\epsilon)}F = E. \tag{2.74}$$

Both $M_\epsilon$ and $M_{inv(\epsilon)}$ have efficient matrix-vector product implementations via FFTs.

The result of Eqs (2.73) and (2.74) can be implemented as a larger linear system in the form of Eq. (2.72). There, the first set of equations, involving the operators I and G, remains untouched. The second set of equations would bring out the relation (2.73) between J on the one hand and E and F on the other, i.e., $C_{11} = j\omega\alpha(M_\epsilon - \epsilon_b I)$, $C_{12} = -I$, and $C_{13} = j\omega(1-\alpha)I$. The third set of equations then relates E and F as in Eq. (2.74), i.e., $C_{21} = -I$, $C_{22} = 0$, and $C_{23} = M_{inv(\epsilon)}$. Finally, the last set of equations, involving $C_{31}$, $C_{32}$, $C_{33}$, last row of the right-hand side would be absent. This may be implemented in calculating electromagnetic scattering properties of a structure, by including numerically solving a volume integral equation for the vector field, F, that is related to and different from the electromagnetic field, E, so as to determine an approximate solution of the vector field, F. Here, the vector field, F, is related to the electric field, E, by the invertible operator $M_{inv(\epsilon)}$.

2.5.2 Concatenated Li Rules

For crossed gratings, Li has shown that the field-material interaction is better captured in a spectral basis when the corresponding interaction matrix is composed of sums of products of (block) Toeplitz and inverse (block) Toeplitz matrices. The (block) Toeplitz matrices allow for efficient matrix-vector products in the fog n of FFTs, but the inverse Toeplitz matrices do not have the Toeplitz form. Therefore, by extending the idea of auxiliary vector fields, we can introduce additional auxiliary fields together with constraints, to arrive at an efficient matrix-vector product that also takes into account the inverse of (block) Toeplitz matrices.

Let us consider the case of isotropic media for a binary grating. Then the Li rules require modifications only for the field components in the transverse plane, i.e., the xy plane. The situation in similar to the case of a single rectangular block, but now we build the permittivity function out of a number of blocks, which may or may not be adjacent. In particular, we write the permittivity function and the corresponding inverse permittivity function as $$\varepsilon = \varepsilon_b \left[ 1 + \sum_{i=1}^{I} \sum_{j=1}^{J} \chi_{i,j} \Pi_i^x(x) \Pi_j^y(y) \right], \tag{2.75}$$

$$\varepsilon^{-1} = \varepsilon_b^{-1} \left[ 1 + \sum_{i=1}^{I} \sum_{j=1}^{J} \hat{\chi}_{i,j} \Pi_i^x(x) \Pi_j^y(y) \right], \tag{2.76}$$

where $\Pi_\alpha^\beta$ is a pulse function in the direction $\beta$ with support on the full interval associated with the label $\alpha$. In the x direction, there are I intervals and in the y direction there are J intervals. Further, $\chi_{i,j}$ are continuous scalar functions on the support of the function $\Pi_i^x(x)\Pi_j^y(y)$, and $\hat{\chi}_{i,j} = -\chi_{i,j}/(1+\chi_{i,j})$.

From the relation $E_x = \epsilon^{-1} D_x$ for the x components of the electric field and flux, we obtain $$E_x = \varepsilon_b^{-1}\left[1 + \sum_{i=1}^{I}\sum_{j=1}^{J} \hat{\chi}_{i,j}\Pi_i^x(x)\Pi_j^y(y)\right]D_x, \qquad (2.77)$$

where, according to Li's line of reasoning, $\Pi_i^x D_x$ is factorizable in Fourier space, but $\Pi_j^y D_x$ is not. Since the functions $\Pi_\alpha^-$ can be interpreted as projection operators, we can employ the following.

Let I be the identity operator and $A_i$ be a sequence of bounded operators that commute with the mutually orthogonal projection operators $P_i$, then the operator $$1 + \sum_{i=1}^{I} A_i P_i$$

has a bounded inverse $$1 + \sum_{i=1}^{I} B_i P_i,$$

where $B_i = -A_i(I+A_i)^{-1}$.

The proof follows by working out the algebra and taking into account the idempotency of the projection operators.

With this result, we can now express the electric flux component in terms of electric field component as $$D_x = \varepsilon_b\left[1 - \sum_{i=1}^{I}\sum_{j=1}^{J}\hat{\chi}_{i,j}\Pi_i^x(x)\Pi_j^y(y)\left(I + \sum_{k=1}^{I}\hat{\chi}_{i,j}\Pi_k^x(x)\right)^{-1}\right]E_x, \qquad (2.78)$$

where the commutation property of $A_i$ and $B_i$ with $P_i$ has been used.

Analogously, we have for they components $$D_y = \varepsilon_b\left[1 - \sum_{i=1}^{I}\sum_{j=1}^{J}\hat{\chi}_{i,j}\Pi_i^x(x)\Pi_j^y(y)\left(I + \sum_{l=1}^{J}\hat{\chi}_{i,l}\Pi_l^y(y)\right)^{-1}\right]E_y. \qquad (2.79)$$

Now each of the multiplication operators are Fourier factorizable after the inverse-matrix operations that operate directly on the components of the electric field have been performed. From these relations, we can derive the contrast current density in the usual way.

From the above relations it becomes clear that every interval along the x and y direction gives rise to an inverse operator, i.e., a total of I+J inverses. Each of these inverses can be avoided if we introduce auxiliary variables (vector fields) to the intermediate matrix-vector products that involve inverse operators, as in the case of a single brick in Section 2.3. In that way, we preserve the efficiency of the matrix-vector product in the form of FFTs, at the expense of more variables. This is especially the case if I and J are larger than 1, since each of the inverses increases the amount of auxiliary variables, thereby increasing the size of the total matrix-vector product.

2.5.3 Reducing the Number of Inverse Operators in the Li Rules

The conclusion of Section 2.5.2 is that each projection operator $\Pi_\alpha^\beta$ introduces a new auxiliary vector field, which makes this procedure rather inefficient for geometries that require more than a few projection operators. Hence, the question arises whether there is a way to work with fewer projection operators than the staircase strategy introduces initially, without sacrificing the geometrical flexibility of this strategy.

The main effort lies in rewriting Eq. (2.75) as a sum that involves fewer projection operators, i.e., to rewrite $$\varepsilon^{-1} = \varepsilon_b^{-1}\left[1 + \sum_{i=1}^{I}\sum_{j=1}^{J}\hat{\chi}_{i,j}\Pi_i^x(x)\Pi_j^y(y)\right]. \qquad (2.80)$$

We are inspired by the famous "four-color problem", which allows a flat map to be colored with only four different colors, such that no two adjacent areas of the map have the same color. In the present case, the situation is somewhat similar: projection operators with adjacent support can only be merged if their multiplying functions $\hat{\chi}_{i,j}$ are continuous across their interconnecting boundary. In general, such constraints are not met by the geometry. Therefore, we introduce a grouping such that we merge projection operators that do not have adjacent supports. This allows us then to construct continuous multiplication operators that match the multiplying functions $\hat{\chi}_{i,j}$ on the support of the merged projection operators.

Let us first demonstrate this in one dimension. Let the (periodic) interval in the x-direction be given as [0,a] and let us divide this interval into an even number of disjoint segments $S_i$ i=0, ..., 2I, such that the union of the segments spans the periodic interval [0,a] and the segments are indexed according to their position along this interval, i.e., segment proceeds segment $S_i$. Then we can write the inverse permittivity function as $$\varepsilon^{-1} = \varepsilon_b^{-1}\left[1 + \sum_{i=1}^{2I}\hat{\chi}_i\Pi_i(x)\right], \qquad (2.81)$$

where the support of $\Pi_i(x)$ corresponds to the ith segment.

Let us now introduce the (mutually orthogonal) odd and even projection operators as $$\Pi_o = \sum_{k=1}^{I}\Pi_{2k-1}(x), \qquad (2.82)$$

$$\Pi_e = \sum_{k=1}^{I}\Pi_{2k}(x). \qquad (2.83)$$

Further, we introduce the (scalar) functions $f_o(x)$ and $f_e(x)$. These functions are continuous on the interval [0,a], have periodic continuity, i.e., $f_o(0)=f_o(a)$ and $f_e(0)=f_e(a)$, and satisfy $$f_o(x)=\hat{\chi}_{2k+1}\ x\in S_{2k+1},$$

$$f_e(x)=\hat{\chi}_{2k}\ x\in S_{2k}, \qquad (2.84)$$

for k=1, ..., I. Owing to the fact that the even and odd projection operators do not merge projection operators with adjacent support, the functions $f_o$ and $f_e$ can be constructed as continuous functions, e.g., via linear interpolation on segments outside the support of the even and odd projection operators. Hence, the inverse permittivity function can be written as $$\epsilon^{-1} = \epsilon_b^{-1}[1 + f_o(x)\Pi_o(x) + f_e(x)\Pi_e(x)]. \quad (2.85)$$

We now extend this idea to two dimensions, i.e., to the transverse plane of the grating structure. We introduce (mutually orthogonal) even and odd projection operators in the x and y direction on a Cartesian product grid with an even number of segments per dimension. Further, we introduce four periodically continuous scalar functions on the periodic domain $[0,a] \times [0,b]$, denoted $f_{oo}(x,y)$, $f_{oe}(x,y)$, $f_{eo}(x,y)$, and $f_{ee}(x,y)$. These functions can be constructed by bi-linear interpolations outside the support of the projection operators by which they are multiplied. The procedure is demonstrated in FIG. 17

Then the inverse permittivity function can be written as $$\epsilon^{-1} = \epsilon_b^{-1}[1 + f_{oo}(x,y)\Pi_o^x(x)\Pi_o^y(y) + f_{oe}(x,y)\Pi_o^x(x)\Pi_e^y(y) + f_{eo}(x,y)\Pi_e^x(x)\Pi_o^y(y) + f_{ee}(x,y)\Pi_e^x(x)\Pi_e^y(y)], \quad (2.86)$$

which shows that there are only four two-dimensional projection operators (colors) involved.

Following the method outlined in Section 2.5.2, we arrive at the following Li rule $$D_x = \epsilon_b\{1 - [f_{oo}(x,y)\Pi_o^y(y) f_{oe}(x,y)\Pi_e^y(y)]\Pi_o^x(x)[I + f_{oo}(x,y)\Pi_o^y(y) + f_{oe}(x,y)\Pi_e^y(y)]^{-1} - [f_{eo}(x,y)\Pi_o^y(y) f_{ee}(x,y)\Pi_e^y(y)]\Pi_e^x(x)[I + f_{eo}(x,y)\Pi_o^y(y) + f_{ee}(x,y)\Pi_e^y(y)]^{-1}\}E_x, \quad (2.87)$$

and a similar expression for the relation between $D_y$ and $E_y$.

To finalize the procedure, we introduce two auxiliary fields $F_e$ and $F_o$, with x components satisfying $$F_x^o(x,y) = [I + f_{oo}(x,y)\Pi_o^y(y) + f_{oe}(x,y)\Pi_e^y(y)]E_x(x,y), \quad (2.88)$$

$$F_x^e(x,y) = [I + f_{eo}(x,y)\Pi_o^y(y) + f_{ee}(x,y)\Pi_e^y(y)]E_x(x,y), \quad (2.89)$$

and similar relations for the y components. With these conditions, we finally obtain $$D_x = \epsilon_b\{E_x - [f_{oo}(x,y)\Pi_o^y(y) + f_{oe}(x,y)\Pi_e^y(y)]\Pi_o^x(x)F_x^o - [f_{eo}(x,y)\Pi_o^y(y) + f_{ee}(x,y)\Pi_e^y(y)]\Pi_e^x(x)F_x^e\}, \quad (2.90)$$

and a similar relation for the y components. Note that the operators that link F and E have a two-dimensional character, as opposed to the inverse operators in the preceding section. Nevertheless, all operators are now multiplication operators that have an efficient matrix-vector product implementation via 2D (or repeated 1D) FFTs.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The methods according to embodiments of the present invention described above may be incorporated into the forward diffraction model for reconstructing an approximate structure of an object (not limited to 1D-periodic) from a detected electromagnetic scattering property, such as a diffraction pattern, arising from illumination of the object by radiation, as described above with reference to FIG. 5. The processing unit PU described above with reference to FIGS. 3 and 4 may be configured to reconstruct an approximate structure of an object using this method.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The term "electromagnetic" encompasses electric and magnetic.

The term "electromagnetic scattering properties" encompasses reflection and transmission coefficients and scatterometry measurement parameters including spectra (such as intensity as a function of wavelength), diffraction patterns (intensity as a function of position/angle) and the relative intensity of transverse magnetic- and transverse electric-polarized light and/or the phase difference between the transverse magnetic- and transverse electric-polarized light. Diffraction patterns themselves may be calculated for example using reflection coefficients.

Thus, although embodiments of the present invention are described in relation to reflective scattering, the invention is also applicable to transmissive scattering.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

All of the following references are incorporated by reference herein in their entireties. [1] M. C. van Beurden and B. P. de Hon. Electromagnetic modelling of antennas mounted on a bandgap slab—discretisation issues and domain and boundary integral equations. In R. D. Graglia, editor, Proceedings of the International Conference on Electromagnetics in Advanced Applications ICEAA '03, pages 637-640. Politecnico di Torino, 2003. [2] Yia-Chung Chang, Guangwei Li, Hanyou Chu, and Jon Opsal. Efficient finite-element, Green's function approach for critical-dimension metrology of three-dimensional gratings on multilayer films. J. Opt. Soc. Am. A, 23(3):638-6454, March 2006. [3] Lifeng Li. Use of Fourier series in the analysis of discontinuous periodic structures. J. Opt. Soc. Am. A, 13(9):1870-1876, September 1996. [4] Lifeng Li. New formulation of the Fourier modal method for crossed surface-relief gratings. J. Opt. Soc. Am. A, 14(10): 2758-2767, October 1997. [5] Philippe Lalanne. Improved formulation of the coupled-wave method for two-dimensional gratings. J. Opt. Soc. Am. A, 14(7):1592-1598, July 1997. [6] Evgeny Popov and Michel Neviere. Maxwell equations in Fourier space: fast-converging formulation for diffraction by arbitrary shaped, periodic, anisotropic media. J. Opt. Soc. Am. A, 18(11):2886-2894, November 2001. [7] Thomas Schuster, Johannes Ruoff, Norbert Kerwien, Stephan Rafler, and Wolfgang Osten. Normal vector method for convergence improvement using the RCWA for crossed gratings. J. Opt. Soc. Am. A, 24(9):2880 {2890, September 2007. [8] Peter Götz, Thomas Schuster, Karsten Frenner, Stephan Rafler, and Wolfgang Osten. Normal vector method for the RCWA with automated vector field generation. OPTICS EXPRESS, 16(22):17295-17301, October 2008.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of reconstructing an approximate structure of an object in an inspection apparatus, the method comprising:
    determining, using a processing device, a model of an electromagnetic scattering property of an estimated structure of the object, the estimated structure being periodic in a direction and comprising materials of differing properties that causes a discontinuity in an electromagnetic field at a material boundary of the estimated structure, wherein the determining comprises:
        numerically solving, using the processing device, a volume integral equation for a vector field to determine an approximate solution of the vector field, the vector field being related to the electromagnetic field by a change of basis and constructed to be continuous at the material boundary, and
        determining, using the processing device, the electromagnetic field from an equation comprising the approximate solution of the vector field;
    detecting an electromagnetic scattering property of the object; and
    comparing, using the processing device, the detected electromagnetic scattering property to the model of the electromagnetic scattering property.

2. The method of claim 1, wherein the electromagnetic scattering properties comprise reflection coefficients.

3. The method of claim 1, wherein the electromagnetic field comprises an incident and a scattered electromagnetic field components.

4. The method of claim 1, wherein:
    the numerically solving of the volume integral equation comprises determining a component of the electromagnetic field by convolution of the vector field with a convolution-and-change-of-basis operator.

5. The method of claim 4, wherein the convolution of the vector field with a convolution-and-change-of-basis operator is performed using a transformation comprising a fast Fourier transform (FFT) or number-theoretic transform (NTT).

6. The method of claim 5, wherein the convolution-and-change-of-basis operator C comprises material and geometric properties of the structure in the direction and is configured to transform the vector field to the electromagnetic field by performing a change of basis according to the material and geometric properties.

7. The method of claim 4, wherein the convolution-and-change-of-basis operator operates according to a finite discrete convolution.

8. The method of claim 4, wherein the numerically solving of the volume integral equation comprises determining a current density by convolution of the vector field with a convolution operator.

9. The method of claim 8, wherein the convolution of the vector field with a convolution operator is performed using a transformation comprising a fast Fourier transform (FFT) or number-theoretic transform (NTT).

10. The method of claim 8, wherein the convolution operator comprises material and geometric properties of the structure in the direction.

11. The method of claim 8, wherein the convolution operator operates according to a finite discrete convolution.

12. The method of claim 8, wherein the current density is a contrast current density.

13. The method of claim 8, wherein the current density is represented by a finite Fourier series with respect to the direction.

14. The method of claim 13, wherein the numerically solving the volume integral equation further comprises determining a scattered electromagnetic field by convolution of the current density with a Green's function operator.

15. The method of claim 14, wherein the convolution of the current density with a Green's function operator is performed using a transformation comprising a fast Fourier transform (FFT) or number-theoretic transform (NTT).

16. The method of claim 1, wherein the vector field is constructed from a combination of field components of the electromagnetic field and a corresponding electromagnetic flux density by using a normal-vector field to filter out continuous components of the electromagnetic field tangential to the material boundary and the continuous components of the electromagnetic flux density normal to the material boundary.

17. The method of claim 1, comprising determining the electromagnetic field by convolution of the approximate solution of the vector field with a convolution-and-change-of-basis operator.

18. The method of claim 17, wherein the convolution is performed using a transformation comprising a fast Fourier transform (FFT) or number-theoretic transform (NTT).

19. The method of claim 1, wherein the vector field is represented by a finite Fourier series with respect to the direction.

20. A method of reconstructing an approximate structure of an object from a detected electromagnetic scattering property arising from illumination of the object by radiation, the method comprising:
   estimating, using a processing device, a structure of the object;
   determining, using the processing device, a model of an electromagnetic scattering property of the estimated structure;
   comparing, using the processing device, the detected electromagnetic scattering property to the model of the electromagnetic scattering property; and
   determining, using the processing device, the approximate structure of the object based on the result of the comparison,
   wherein the model of the electromagnetic scattering property is determined by calculating an electromagnetic scattering property of the estimated structure, the estimated structure being periodic in a direction and comprising materials of differing properties that causes a discontinuity in an electromagnetic field at a material boundary, the calculating comprising:
      numerically solving, using the processing device, a volume integral equation for a vector field to determine an approximate solution of the vector field, the vector field being related to the electromagnetic field by a change of basis and constructed to be continuous at the material boundary; and
      determining, using the processing device, the electromagnetic field from an equation comprising the approximate solution of the vector field.

21. The method of claim 20, further comprising:
   storing a plurality of additional models of the electromagnetic scattering property in a library, wherein each of the plurality of additional models correspond to an estimated structure of a plurality of additional structures of the object; and
   comparing the detected electromagnetic scattering property to contents of the library.

22. The method of claim 20, further comprising:
   iterating the estimating of the structure, the determining of the model, and the comparing of the detected electromagnetic scattering to the model,
   wherein the estimating of the structure is based on a result of the comparing from a previous iteration.

23. An inspection apparatus for reconstructing an approximate structure of an object, the inspection apparatus comprising:
   an illumination system configured to illuminate the object with radiation;
   a detection system configured to detect an electromagnetic scattering property arising from the illumination; and
   a processor configured to:
      estimate a structure of the object, the estimated structure being periodic in a direction and comprising materials of differing properties that causes a discontinuity in an electromagnetic field at a material boundary of the estimated structure;
      determine a model of an electromagnetic scattering property of the estimated structure;
      compare the detected electromagnetic scattering property to the model of the electromagnetic scattering property; and
      determine the approximate structure of the object from a difference between the detected electromagnetic scattering property and the model of the electromagnetic scattering property,
      wherein the processor is configured to determine the model electromagnetic scattering property by:
         numerically solving a volume integral equation for a vector field to determine an approximate solution of the vector field, the vector field being related to the electromagnetic field by a change of basis and constructed to be continuous at the material boundary;
         determining the electromagnetic field from an equation comprising the approximate solution of the vector field; and
         determining the electromagnetic scattering properties from the determined electromagnetic field.

24. A non-transitory machine-readable storage medium containing instructions, the instructions being executable by a computing device for causing the computing device to perform a method for determining a model of a first electromagnetic scattering property of a structure of an object, the method comprising:
   calculating electromagnetic scattering properties of a structure, the structure being periodic in a direction and comprising materials of differing properties that causes a discontinuity in an electromagnetic field at a material boundary of the structure, the calculating comprising:
      numerically solving a volume integral equation for a vector field to determine an approximate solution of the vector field, the vector field being related to the electromagnetic field by a change of basis and constructed to be continuous at the material boundary; and
      determining the electromagnetic field from an equation comprising the approximate solution of the vector field.

25. The method of claim 24, wherein the vector field is related to the electromagnetic field by an invertible operator.

* * * * *